(12) United States Patent
Yayon et al.

(10) Patent No.: US 9,610,357 B2
(45) Date of Patent: *Apr. 4, 2017

(54) CONJUGATES OF CARBOXY POLYSACCHARIDES WITH FIBROBLAST GROWTH FACTORS AND VARIANTS THEREOF

(71) Applicant: HEPACORE LTD., Ness Ziona (IL)

(72) Inventors: Avner Yayon, Moshav Sitria (IL); Roy Sirkis, Ness Ziona (IL); Boaz Amit, Kiryat Ono (IL); Avraham Wortzel, Rishon le Zion (IL)

(73) Assignee: HEPACORE LTD., Ness Ziona (IL)

(*) Notice: Subject to any disclaimer, the term of this patent is extended or adjusted under 35 U.S.C. 154(b) by 0 days.

This patent is subject to a terminal disclaimer.

(21) Appl. No.: 14/054,300

(22) Filed: Oct. 15, 2013

(65) Prior Publication Data

US 2014/0038892 A1 Feb. 6, 2014

Related U.S. Application Data

(63) Continuation of application No. PCT/IL2012/000158, filed on Apr. 5, 2012.

(60) Provisional application No. 61/474,299, filed on Apr. 12, 2011.

(51) Int. Cl.
| | |
|---|---|
| *C07K 14/50* | (2006.01) |
| *A61K 38/18* | (2006.01) |
| *A61K 47/48* | (2006.01) |
| *A61K 38/36* | (2006.01) |

(52) U.S. Cl.
CPC ...... *A61K 47/4823* (2013.01); *A61K 38/1825* (2013.01); *A61K 38/363* (2013.01); *C07K 14/50* (2013.01)

(58) Field of Classification Search
CPC .............. A61K 47/4823; A61K 38/363; A61K 38/1825; C07K 14/50
See application file for complete search history.

(56) References Cited

U.S. PATENT DOCUMENTS

| | | | |
|---|---|---|---|
| 2,492,458 A | 12/1949 | Bering | |
| 4,582,865 A | 4/1986 | Balazs et al. | |
| 4,642,120 A | 2/1987 | Nevo et al. | |
| 4,713,448 A | 12/1987 | Balazs et al. | |
| 5,128,326 A | 7/1992 | Balazs et al. | |
| 5,209,776 A | 5/1993 | Bass et al. | |
| 5,260,420 A | 11/1993 | Burnouf-Radosevich et al. | |
| 5,290,918 A | 3/1994 | Bui-Khac | |
| 5,411,885 A | 5/1995 | Marx | |
| 5,512,460 A | 4/1996 | Nauro et al. | |
| 5,571,895 A | 11/1996 | Kurokawa et al. | |
| 5,616,568 A | 4/1997 | Pouyani et al. | |
| 5,631,011 A | 5/1997 | Wadstrom | |
| 5,760,200 A | 6/1998 | Miller et al. | |
| 5,763,410 A | 6/1998 | Edwardson et al. | |
| 5,856,299 A | 1/1999 | Righetto et al. | |
| 5,874,417 A | 2/1999 | Prestwich et al. | |
| 5,972,385 A | 10/1999 | Liu et al. | |
| 5,998,170 A | 12/1999 | Arakawa et al. | |
| 6,030,958 A | 2/2000 | Burns et al. | |
| 6,074,663 A | 6/2000 | Delmotte et al. | |
| 6,174,999 B1 | 1/2001 | Miller et al. | |
| 6,274,090 B1 | 8/2001 | Coelho et al. | |
| 6,288,043 B1 | 9/2001 | Spiro et al. | |
| 6,310,267 B1 | 10/2001 | Rapp | |
| 6,334,968 B1 | 1/2002 | Shapiro et al. | |
| 6,398,816 B1 | 6/2002 | Breitbart et al. | |
| 6,425,918 B1 | 7/2002 | Shapiro et al. | |
| 6,440,427 B1 | 8/2002 | Wadstrom | |
| 6,482,231 B1 | 11/2002 | Abatangelo et al. | |
| 6,486,377 B2 | 11/2002 | Rapp | |
| 6,503,527 B1 | 1/2003 | Whitmore et al. | |
| 6,630,457 B1 | 10/2003 | Aeschlimann et al. | |
| 6,699,484 B2 | 3/2004 | Whitmore et al. | |
| 6,943,154 B2 | 9/2005 | Miller et al. | |
| 7,009,039 B2 | 3/2006 | Yayon et al. | |
| 7,034,127 B2 | 4/2006 | Parent et al. | |
| 7,749,965 B2 * | 7/2010 | Moore ................. | A61K 31/722 424/423 |
| 8,623,820 B2 * | 1/2014 | Pickering ........... | A61K 31/7088 514/13.3 |
| 9,226,949 B2 * | 1/2016 | Yayon ................ | A61K 38/1825 |
| 2004/0014658 A1 | 1/2004 | Bogin et al. | |
| 2004/0120993 A1 | 6/2004 | Zhang et al. | |
| 2004/0136952 A1 | 7/2004 | Bhaskaran et al. | |

(Continued)

FOREIGN PATENT DOCUMENTS

| | | |
|---|---|---|
| EP | 0111311 A2 | 6/1984 |
| EP | 0325270 A2 | 7/1989 |

(Continued)

OTHER PUBLICATIONS

Almany and Seliktar (2005) Biosynthetic hydrogel scaffolds made from fibrinogen and polyethylene glycol for 3D cell cultures. Biomaterials 26(5): 2467-2477.

Bellosta et al., (2001) Identification of receptor and heparin binding sites in fibroblast growth factor 4 by structure-based mutagenesis. Mol Cell Biol 21(17): 5946-5957.

Bencherif et al., (2008) Influence of the degree of methacrylation on hyaluronic acid hydrogels properties. Biomaterials 29(12): 1739-1749.

Bulpitt and Aeschlimann (1999) New strategy for chemical modification of hyaluronic acid: preparation of functionalized derivatives and their use in the formation of novel biocompatible hydrogels. J Biomed Mater Res 47(2): 152-169.

Davidson et al., (2005) Fibroblast growth factor (FGF) 18 signals through FGF receptor 3 to promote chondrogenesis. J Biol Chem 280(21): 20509-20515.

(Continued)

*Primary Examiner* — Marianne P Allen

(74) *Attorney, Agent, or Firm* — Vorys, Sater, Seymour & Pease LLP

(57) ABSTRACT

Conjugates of hydrophilic carboxy polysaccharides with protein members of the fibroblast growth factor (FGF) family and variants thereof. The conjugates provide a modified bioactivity and stability of FGFs for various therapeutic applications.

8 Claims, 8 Drawing Sheets

(56) References Cited

U.S. PATENT DOCUMENTS

| | | | |
|---|---|---|---|
| 2004/0176295 | A1 | 9/2004 | Radomsky |
| 2005/0142163 | A1 | 6/2005 | Hunter et al. |
| 2006/0159733 | A1 | 7/2006 | Pendharkar et al. |
| 2008/0176790 | A1 | 7/2008 | DeFrees |
| 2008/0193425 | A1 | 8/2008 | Ellsworth |
| 2008/0255045 | A1* | 10/2008 | Cujec et al. ............ 514/12 |
| 2009/0111748 | A1* | 4/2009 | Ellerby et al. ............ 514/12 |
| 2009/0247462 | A1 | 10/2009 | Bogin et al. |
| 2009/0286965 | A1 | 11/2009 | Imamura et al. |
| 2010/0016223 | A1 | 1/2010 | Gimona et al. |
| 2010/0086594 | A1* | 4/2010 | Amit et al. ............ 424/484 |
| 2010/0125049 | A1 | 5/2010 | Bossard et al. |
| 2010/0210509 | A1 | 8/2010 | Oh et al. |
| 2011/0015345 | A1 | 1/2011 | Pinkstaff et al. |
| 2011/0053841 | A1 | 3/2011 | Yayon et al. |
| 2011/0091443 | A1 | 4/2011 | Kim et al. |
| 2011/0212901 | A1 | 9/2011 | Akiyoshi et al. |

FOREIGN PATENT DOCUMENTS

| | | | |
|---|---|---|---|
| EP | 1790665 | A1 | 5/2007 |
| JP | S60101101 | A | 6/1985 |
| WO | 9220349 | A1 | 11/1992 |
| WO | 9524429 | A1 | 9/1995 |
| WO | 9915209 | A2 | 4/1999 |
| WO | 0001733 | A1 | 1/2000 |
| WO | 0016818 | A1 | 3/2000 |
| WO | 0051538 | A1 | 9/2000 |
| WO | 0105434 | A2 | 1/2001 |
| WO | 0139788 | A2 | 6/2001 |
| WO | 0160412 | A2 | 8/2001 |
| WO | 0236732 | A2 | 5/2002 |
| WO | 02100440 | A1 | 12/2002 |
| WO | 03007873 | A2 | 1/2003 |
| WO | 03087160 | A1 | 10/2003 |
| WO | 03094835 | A2 | 11/2003 |
| WO | 2004067704 | A2 | 8/2004 |
| WO | 2006063362 | A1 | 6/2006 |
| WO | 2007026362 | A2 | 3/2007 |
| WO | WO 2007/102149 | * | 9/2007 |
| WO | 2008038287 | A2 | 4/2008 |
| WO | 2008081463 | A2 | 7/2008 |
| WO | WO 2009/120893 | * | 10/2009 |
| WO | 2012038953 | A2 | 3/2012 |

OTHER PUBLICATIONS

Duncan et al., (2008) Polymer masked-unmasked protein therapy. 1. Bioresponsive dextrin-trypsin and -melanocyte stimulating hormone conjugates designed for alpha-amylase activation. Biomacromolecules 9(4): 1146-1154.

Fantl and Ward (1965) Molecular weight of human fibrinogen derived from phosphorus determinations. Biochem J 96(3): 886-889.

Ferguson and Duncan (2009) Dextrin-phospholipase A2: synthesis and evaluation as a bioresponsive anticancer conjugate. Biomacromolecules 10(6): 1358-1364.

Ferguson et al., (2010) Evaluation of hyaluronic acid-protein conjugates for polymer masked-unmasked protein therapy. Int J Pharam 402(1-2): 95-102.

Gilles et al., (1990) Stability of water-soluble carbodiimides in aqueous solution. Anal Biochem 184(2): 244-248.

Haisch et al., (2000) Preparation of a pure autologous biodegradable fibrin matrix for tissue engineering. Med Biol Eng Comput (Cell Eng) 38(6): 686-689.

Hamidouche et al., (2010) Autocrine fibroblast growth factor 18 mediates dexamethasone-induced osteogenic differentiation of murine mesenchymal stem cells. J Cell Physiol 224(2): 509-515.

Hardwicke et al., (2008) Dextrin-rhEGF conjugates as bioresponsive nanomedicines for wound repair. J Control Release 130(3): 275-283.

Imamura et al., (1990) Recovery of mitogenic activity of a growth factor mutant with a nuclear translocation sequence. Science 249(4976): 1567-1570.

Itokazu et al., (1997) The sustained release of antibiotic from freeze-dried fibrin-antibiotic compound and efficacies in a rat model of osteomyelitis. Infection 25(6): 359-363.

Kang et al., (2010) Poly(ethylene glycol) modification enhances penetration of fibroblast growth factor 2 to injured spinal cord tissue from an intrathecal delivery system. J Control Release 144(1): 25-31.

Kim et al., (2009) Characterization of low-molecular-weight hyaluronic acid-based hydrogel and differential stem cell responses in the hydrogel microenvironments. J Biomed Mater Res A 88(4): 967-975.

Kong et al., (2010) Long acting hyaluronate—exendin 4 conjugate for the treatment of type 2 diabetes. Biomaterials 31(14): 4121-4128.

Kuroda et al., (1999) Anabolic effect of aminoterminally truncated fibroblast growth factor 4 (FGF4) on bone. Bone 25(4): 431-437.

LeBoeuf et al., (1986) Human fibrinogen specifically binds hyaluronic acid. J Biol Chem 261(27): 12586-12592.

LeBoeuf et al., (1987) Effects of hyaluronic acid and other glycosaminoglycans on fibrin polymer formation. Biochem 26(19): 6052-6057.

Li et al., (2004) Synthesis and biological evaluation of a crosslinked hyaluronan-mitomycin C hydrogel. Biomacromol 5(3): 895-902.

Liu et al., (2002) Hyaluronate-heparin conjugate gels for the delivery of basic fibroblast growth factor (FGF-2). J Biomed Mater Res 62(1): 128-135.

Luo and Prestwich (2001) Hyaluronic Acid-N-hydroxysuccinimide: A Useful Intermediate for Bioconjugation. Bioconj Chem 12(6): 1085-1088.

McKee et al., (1970) Subunit structure of human fibrinogen, soluble fibrin, and cross-linked insoluble fibrin. Proc Natl Acad Sci 66(3): 738-744.

Meléndez-Alafort et al., (2009) Biokinetic and dosimetric studies of 188Re-hyaluronic acid: a new radiopharmaceutical for treatment of hepatocellular carcinoma. Nucl Med Biol 36(6): 693-701.

Miyaoka et al, (2010) A novel regulatory mechanism for Fgf18 signaling involving cysteine-rich FGF receptor (Cfr) and delta-like protein (Dlk). Development 137(1): 159-167.

Mohammadi et al., (2005) Structural basis for fibroblast growth factor receptor activation. Cytokine Growth Factor 16(2): 107-137.

Nakaji-Hirabayashi et al., (2009) Hyaluronic acid hydrogel loaded with genetically-engineered brain-derived neurotrophic factor as a neural cell carrier. Biomaterials 30(27): 4581-4589.

Oh et al., (2008) Signal transduction of hyaluronic acid-peptide conjugate for formyl peptide receptor like 1 receptor. Bioconjug Chem 19(12): 2401-2408.

Oh et al., (2009) Synthesis, characterization, and preliminary assessment of anti-Flt1 peptide-hyaluronate conjugate for the treatment of corneal neovascularization. Biokmaterials 30(30): 6026-6034.

Olsen et al., (2004) Insights into the molecular basis for fibroblast growth factor receptor autoinhibition and ligand-binding promiscuity. PNAS 101(4): 935-940.

Ornitz (2000) FGFs, heparan sulfate and FGFRs: complex interactions essential for development. Bioassays 22(2): 108-112.

Ornitz and Itoh (2001) Fibroblast growth factors. Gen Biol 2(3): 3005.1-3005.12.

Plotnikov et al., (2000) Crystal structures of two FGF-FGFR complexes reveal the determinants of ligand-receptor specificity. Cell 101: 413-424.

Pouyani and Prestwich (1994) Functionalized Derivatives of Hyaluronic Acid Oligosaccharides: Drug Carriers and Novel Biomaterials. Bioconj Chem 5(4): 339-347.

Prestwich (2001) Biomaterials From Chemically-Modified Hyaluronan. Glycoforum. http://www.glycoforum.gr.jp/science/hyaluronan/HA18/HA18E.html; Retrieved from the Internet on Jan. 20, 2011.

Prestwich et al., (1998) Controlled chemical modification of hyaluronic acid: synthesis, applications, and biodegradation of hydrazide derivatives. J Cont Release 53: 93-103.

Saik et al., (2011) Covalently immobilized platelet-derived growth factor-BB promotes angiogenesis in biomimetic poly (ethylene glycol) hydrogels. Acta Biomater 7(1): 133•143.

(56) References Cited

OTHER PUBLICATIONS

Sakurai et al., (1997) Anti-inflammatory activity of superoxide dismutase conjugated with sodium hyaluronate. Glycoconj J 14(6): 723-728.

Seno et al., (1990) Carboxyl-terminal structure of basic fibroblast growth factor significantly contributes to its affinity for heparin. Eur J Biochem 188(2): 239-245.

Shu et al., (2004) Attachment and spreading of fibroblasts on an RGD peptide-modified injectable hyaluronan hydrogel. J Biomed Mat Res 68A(2): 365-375.

Solchaga et al., (1999) Hyaluronic Acid-B ased Polymers as Cell Carriers for Tissue-Engineered Repair of Bone and Cartilage. J Orthop Res 17(2): 205-213.

Sun et al., (2010) Cytokine binding by polysaccharide-antibody conjugates. Mol Pharm 7(5): 1769-1777.

Tanaka et al., (1995) Human androgen-induced growth factor in prostate and breast cancer cells: its molecular cloning and growth properties. FEBS Lett 363(3): 226-230.

Thomas et al., (2010) Dendrimer-based tumor cell targeting of fibroblast growth factor-1. Bioorg Med Chem Lett 20(2): 700-703.

Trudel et al., (2006) The inhibitory anti-FGFR3 antibody, PRO-001, is cytotoxic to t(4;14) multiple myeloma cells. Blood 107(1): 4039-4046.

Wu et al., (2006) Site-directed PEGylation of human basic fibroblast growth factor. Protein Expr Purif 48(1): 24-27.

Wu et al., (2007) Purification and modification by polyethylene glycol of a new human basic fibroblast growth factor mutant-hbFGF(Ser25,87,92). J Chromatogr A 1161(1-2): 51-55.

Yamaguchi and Kiick (2005) Polysaccharide-poly(ethylene glycol) star copolymer as a scaffold for the production of bioactive hydrogels. Biomacromolecules 6(4): 1921-1930.

Zhang et al., (2006) Receptor specificity of the fibroblast growth factor family. The complete mammalian FGF family. J Biol Chem 281(23): 15694-15700.

\* cited by examiner

CONJUGATES OF CARBOXY POLYSACCHARIDES WITH FIBROBLAST GROWTH FACTORS AND VARIANTS THEREOF

FIELD OF THE INVENTION

The present invention relates to conjugates of hydrophilic carboxy polysaccharides covalently coupled with protein members of the fibroblast growth factor (FGF) family and variants thereof. The conjugates provide a modified bioactivity and stability of FGFs for various therapeutic applications.

BACKGROUND OF THE INVENTION

Polymer-protein conjugation, particularly conjugation with polyethylene glycol (also known as PEGylation), is a well-established mean for increasing the circulation time, reducing antigenicity and improving the stability of proteins. Conjugation thus often leads to improved therapeutic benefits of the proteins as compared to non-conjugated proteins. Conjugation of proteins with polyethylene glycol (PEG) was shown to be applicable for various clinical uses (Duncan et al. Biomacromol., 2008, 9, 1146-1154).

Conjugation of FGF2 with PEG was described in Saik et al. (Acta Biomateri., 2011, 7, 133-143). Using an injured spinal cord model, the local administration of an FGF2-PEG conjugate provided an improved tissue penetration of the FGF2 (Kang et al, J. Cont. Release, 2010, 144, 25-31). Wu et al. (Prot. Expr. and Puri., 2006, 48, 24-27 and J. Chrom. A, 2007, 1161, 51-55) described the conjugation of PEG with modified FGF2 in which 3 out of 4 cysteine residues were replaced by serine residues. In these studies, the PEG-modified FGF2 conjugate retained the heparin binding capabilities of the modified FGF2 and partly retained its mitogenic activity. The conjugate also gained heat stability. US patent application No. 2004/0136952 discloses a method of synthesizing conjugates of synthetic water-soluble polymers with certain bioactive components, which conjugates retain high receptor binding activity. Specifically conjugates of PEG with Interferon-alpha, Interleukin-2, EGF and TGF-1 were disclosed. Conjugation of modified FGF21 with PEG was disclosed in U.S. patent application No. 2008/0255045. FGF21 was modified by introducing substitutions with unnatural amino acids that enabled its conjugation with azido-PEG. The pharmacokinetic profile of conjugated FGF21 was significantly improved as compared to non-conjugated FGF21. Conjugation of FGF1 with G5-polyamidoamine dendrimer was described in Thomas et al. (Bioorg. Med. Chem. Lett., 2010, 20(2), 700-703). It was suggested that multivalent G5-FGF nanoparticles may serve as a platform for cytosolic as well as nuclear drug delivery into tumor cells, and as an FGF delivery agent for inducing angiogenesis during wound healing.

Despite the advantages of conjugating proteins with polymers such as PEG, repeated administration of such conjugates was shown to result in the accumulation of the administered conjugate, mainly due to non-biodegradability of the polymers. The accumulation may lead to some potential problems including vacuolization, lysosomal storage diseases and, at high concentration, may also induce other pathological metabolic changes (Ferguson, Inter. J. Pharamc., 2010, 402(1-2), 95-102).

Hyaluronic Acid (HA)

Hyaluronic acid (hyaluronan, HA) is a glycosaminoglycan found in the extracellular matrix of all connective tissues. HA is known to bind specifically proteins in the extracellular matrix and on the cell surface. The unique viscoelastic properties of HA combined with its biocompatibility, immunoneutrality and its biodegradability has led to its use in a variety of clinical applications such as eye surgery and visco-supplementation of joints.

HA was implicated for utility as a carrier of cells, or growth factors for applications of bone deficiencies. US patent application No. 2004/0176295 provides a bone growth composition comprising a mixture of HA and an FGF. US patent application No. 2008/0193425 discloses that when hyaluronic acid is administered in addition to FGF18, the effects on chondrocyte proliferation and production of matrix were found to be greater than administration of FGF18 or hyaluronic acid alone. Prestwich (Biomaterials from Chemically modified Hyaluronan, Glycoforum; http://www.glycoforum.gr.jp/science/hyaluronan/HA18/HA18E.html) discussed the conjugation of hyaluronic acid with drugs (e.g. Taxol®). US patent application No. 2011/0212901 provides a hydrophobic group-introduced into HA derivative and a pharmaceutical composition comprising same. Conjugation of HA with peptide agonists of Formyl peptide receptor-like 1 (FPRL1) for increasing their half life circulation and/or their bioavailability was disclosed in Oh et al. (Bioconjugate Chem., 2008, 19, 2401-2408). In another study, HA was conjugated to anti-flt1 peptide (Oh et al, Biokmaterials, 2009, 20, 6026-6034). J-Hyun Kong et al. (Biomaterials, 2010, 31, 4121-4128) described the conjugation of HA with exendin 4 (Byetta®), a 39 amino acid peptide which was exploited for the treatment of type 2 diabetes. In this study, the in vitro serum stability of exendin 4 was improved by a factor of 20 while maintaining its biological activities. U.S. Pat. No. 7,034,127 disclosed methods of conjugating biologically active substances, particularly α-interferon, with HA. The HA-interferon conjugate was biologically active. Further disclosed in U.S. Pat. No. 7,034,127 is the preparation of HA conjugates with epidermal growth factor (EGF), anti-BSA antibody, cytochrome C and avidin. Liu et al. (J Biomed Mater. Res., 2002, 62(1): 128-35) demonstrated hyaluronate-heparin conjugate gels for the delivery of FGF-2. U.S. Pat. No. 6,288,043 to Liu et al. disclosed an injectable composition for promoting bone and/or cartilage growth comprising hyaluronate-heparin conjugates. These conjugates have inherent binding sites for members of the FGF family. Ferguson, (Inter. J. Pharm., 2010, 402(1-2), 95-102) demonstrated the conjugation of HA with EGF with a very low yield (12%). The conjugate was inactive, even after treatment with hyaluronidase which degrades HA. In the same study, HA-trypsin conjugate retained its activity. WO 2001/05434 disclosed the conjugation of HA with Interleukin-1 (Il-1) receptor antagonist, osteoprotegrin and leptin. Several protein conjugates showed improved efficacy, longer circulation time, higher water solubility and reduction in adverse injection site reactions. Interlukin-1β and tumor necrosis factor monoclonal antibodies were covalently modified with HA and carboxy methyl cellulose (CMC). These conjugates were capable of binding pro-inflammatory cytokines (Sun et al, Mol. Pharma., 2010, 7, 1769-1777). EP 1790665 disclosed a process for producing water-soluble HA modification. Further disclosed is a conjugate of the modified HA with a drug, a protein, a peptide, a nucleic acid, or a low-molecular-weight compound including IgG Fab and GLP-1. WO 2008/081463 to some of the inventors of the present application discloses the water-soluble reactive esters of carboxy polysaccharides and derivatives thereof and the formation of water-soluble covalent fibrinogen conjugates, including HA-fibrinogen conjugates. In an effort to obtain long-acting formulation of biopharmaceuticals, US patent application No. 2010/0210509 discloses a long acting conjugate of peptide with HA derivative having a long-term stability and a high efficacy, and a method of preparing said conjugate.

Fibroblast Growth Factors

Fibroblast growth factors (FGFs) comprise a large family of evolutionarily conserved polypeptides involved in a variety of biological processes including morphogenesis, angiogenesis, and tissue remodeling as well as in the pathogenesis of numerous diseases. The various members of this family stimulate the proliferation of a wide spectrum of cells, including those deriving from mesenchymal, endothelial, epithelial and neuroectodermal origin. FGFs are expressed in a strict temporal and spatial pattern during development and have important roles in patterning and limb formation (Ornitz, Bioassays, 2000, 22, 108-112). All members of the FGF family share a homology core domain of about 120 amino acids, 28 aa residues are highly conserved and four are identical. The adjacent N- and C-termini are of variable length and share limited homology. The core domain comprises both the primary receptor binding sites and a heparin-binding domain, which are distinct from each other (Ornitz et al, Gen. Biol., 2001, 2(3), 3005.1-3005.12). Because of their wide ranging and potent activities, FGFs are pursued as therapeutic agents for a number of different indications, including wound healing, bone fractures, skin conditions, tissue protection, repair, and the induction of angiogenesis during myocardial infarction and ischemia, inflammatory conditions, neurological conditions, and diabetes. WO 2012/038953 to some of the inventors of the present application discloses FGF-18 variants having increased receptor specificity for cartilage repair and treatment of degenerative joint disease.

FGFs were previously conjugated or incorporated into drug delivery systems. US patent application No. 2008/0176790 discloses conjugates of modified FGF peptides, particularly FGF20 and FGF21 peptides with PEG polymer. The FGF peptides are modified with N-linked or O-linked glycosylation site(s). US patent application No. 2011/0015345 discloses modified FGF-23 polypeptides linked to a water-soluble polymer, particularly PEG.

There remains an unmet need for FGFs with sustained release or prolonged effects for use for example in wound healing, osteoarthritis or bone repair conjugates. These attributes are provided by conjugates of FGFs with carboxy polysaccharides, particularly HA, which provide improved bioactivity and stability of the FGFs for various therapeutic applications.

SUMMARY OF THE INVENTION

The present invention provides conjugates of carboxy polysaccharides covalently bound to FGFs or variants thereof. The conjugates provide improved biological activities especially in affording sustained release or prolonged activity in vivo. The conjugates are useful for treatment of indications in which FGFs possesses therapeutic activity including, but not limited to wound healing and especially for orthopedic indications. According to certain embodiments the conjugates further comprise fibrin(ogen) (FBN), thereby providing a triple conjugate.

The present invention further provides methods of preparing the conjugates by amide bond formation between the amino group of the fibrin(ogen) or FGFs or variants thereof and activated carboxylic moieties of the carboxy polysaccharides or by the formation of a carbon-sulfur bond via a Michael addition of the FGF thiol groups to a Michael acceptor-derivatized carboxy polysaccharide.

According to a specific embodiment, the FGFs or variants thereof are coupled with the carboxy polysaccharide hyaluronic acid (HA). Unexpectedly, the FGFs or variants thereof are efficiently and quantitatively conjugated with HA either directly or via a linker, thereby producing extremely high yield of conjugate product following synthesis reactions as opposed to other growth factors, such as Epidermal Growth Factor (EGF) which are conjugated with HA in significantly less efficient manner.

The present invention overcomes drawbacks of known compositions and methods. The limitations of injecting FGFs, like many other growth factors, include a short plasma half-life, poor stability and, immunogenicity. The conjugates of the present invention display improved characteristics which overcome the known limitations associated with non-conjugated FGFs. As exemplified herein, the conjugates of the present invention retained mitogenic activity on primary articular chondrocytes and other cell lines and demonstrated improved activity in vivo in animal models. Moreover, the conjugates demonstrated prolonged stability by achieving efficient therapeutic outcomes with a single administration as opposed to non-conjugated FGFs which necessitated multiple, frequent administrations. Thus, the reduced treatment regimes render the conjugates of the present invention particularly advantageous since less frequent dosing is of great benefit to the patients.

Taken together, the conjugates of the present invention provide improved activity and stability of the FGFs and require less frequent dosing. Moreover, conjugation of FGF with the carboxy polysaccharide can provide reduced immunogenicity and/or prolonged plasma half-life which might afford efficient activity upon injection systemically into the blood circulation.

According to one aspect, the present invention provides a conjugate comprising a fibroblast growth factor (FGF) or variant thereof covalently coupled to a carboxy polysaccharide. According to some embodiments, the FGF or variant thereof can be coupled to the carboxy polysaccharide either directly or via a linker. According to some embodiments, the carboxy polysaccharide and FGF or variant thereof are coupled via an amide bond between a carboxylic functional group of said carboxy polysaccharide and an amino functional group of said FGF or a variant thereof.

According to other embodiments, the FGF or variant thereof is covalently coupled to a carboxy polysaccharide via a linker, thereby providing the modified release of active FGF or a variant thereof. According to some embodiments, the linker comprises a hydrazido moiety coupled to a moiety selected from the group consisting of a maleimido moiety or a vinyl sulfone moiety. According to some embodiments, the linker is a biodegradable linker. According to some embodiments, the linker is for example a pH-sensitive linker or an enzymatically-cleavable linker. According to some embodiments, the modified release of active FGF or a variant thereof is provided by at least one of the following mechanisms:
  a) hydrolyzing the carboxy polysaccharide;
  b) degrading the carboxy polysaccharide with an enzyme;
  c) degrading the carboxy polysaccharide by reactive oxidative species; or
  d) degrading the linker by, for example an enzyme or hydrolysis.

Each possibility represents a separate embodiment of the present invention.

According to some embodiments, the conjugate of FGF or variant thereof and carboxy polysaccharide further comprises fibrin(ogen), thereby providing a triple conjugate. According to some embodiments, the fibrin(ogen) can be coupled to the carboxy polysaccharide either directly or via a linker. According to some embodiments, the fibrin(ogen) and FGF or variant thereof are coupled to the carboxy polysaccharide via an amide bond between a carboxylic functional group of said carboxy polysaccharide and an amino functional group of said fibrin(ogen).

The FGF of the obtained conjugates can be active either in its conjugated form or upon enzymatic degradation of the carboxy polysaccharide moiety, or linker. According to some embodiments, the conjugates provide FGF or variants thereof activities which are substantially similar to the activities of non-conjugated FGFs, but may be advantageous in that they are more selective or more effective or longer acting. According to some embodiments, the conjugates provide FGF or variants thereof activity of at least 50% of the activity of non-conjugated FGF or variant thereof. According to some embodiments, the conjugates provide FGF or variants thereof activity of at least 80% of the activity of non-conjugated FGF or variant thereof. According to yet other embodiments, the conjugates provide FGF or variant thereof activity greater than the activity of non-conjugated FGF or variant thereof.

According to some embodiments, the conjugates are administered locally into an area of defect or disease where they act more potently than the non-conjugated FGFs or variants thereof. According to some embodiments, more potently refers to a more prolonged activity thus decreasing the number of administrations required to achieve a given effect. According to other embodiments the term more potently refers to a more selective activity on target cell types.

According to some embodiments, the fibrin(ogen) is mammalian or non-mammalian fibrinogen. According to some embodiments, fibrinogen is for example, human, bovine, equine, ovine or porcine fibrinogen. According to certain embodiments, fibrinogen is human fibrinogen. According to some embodiments, fibrinogen is a natural fibrinogen isolated, for example, from donor plasma or recombinant fibrinogen. According to some embodiments, the fibrin(ogen) is cleaved to fibrin by a fibrinogen cleaving agent, thereby producing a water insoluble clot. According to some embodiments, the fibrinogen cleaving agent is for example thrombin. According to some embodiments, the fibrin clot can be produced ex vivo or in situ. According to some embodiments, the clot is freeze-dried, thereby producing a porous matrix or scaffold.

According to additional embodiments, the carboxy polysaccharide is selected from the group consisting of a natural polysaccharide, a synthetic polysaccharide, a semi-synthetic polysaccharide, and combinations thereof. Each possibility represents a separate embodiment of the present invention.

Natural polysaccharides include, but are not limited to, glycosaminoglycans, alginate, fucoidan, galactans, galactomannans, glucomannans, xanthan gum, gellan and Poly sialic acid (PSA).

Glycosaminoglycans include, but are not limited to, hyaluronic acid, heparin, chondroitin sulfate, dermatan sulfate, heparan sulfate, keratan sulfate, and combinations thereof. Each possibility represents a separate embodiment of the present invention. Derivatives and salts of the above, including low molecular weight forms of the glycosaminoglycans are intended to be included in the invention.

Semi-synthetic carboxy polysaccharides include, but are not limited to, carboxyalkyl derivatives of cellulose, starch and chitin, for example, carboxymethylcellulose (CMC). Each possibility represents a separate embodiment of the present invention.

According to one embodiment, the carboxy polysaccharide is hyaluronic acid (HA) and its derivatives including, but not limited to, the partial esters of hyaluronic acid with aliphatic, aryliphatic, heterocyclic and cycloaliphatic alcohols. Each possibility represents a separate embodiment of the present invention. Suitable molecular weights of hyaluronic acid and its partial esters range from about $10^4$ Daltons to about three million ($3\times10^6$) Daltons. In accordance with these embodiments, the enzyme which affords the sustained release of active FGF or a variant thereof is hyaluronidase.

According to further embodiments, the FGF is selected from mammalian and non-mammalian FGF. According to some embodiments, the FGF is human, bovine, equine, ovine porcine or rodent FGF. Each possibility represents a separate embodiment of the present invention. In certain embodiments, the FGF is selected from FGF-18, FGF-2, FGF-1, FGF-3, FGF-4, FGF-5, FGF-6, FGF-7, FGF-8, FGF-9, FGF-10, FGF-15, FGF-16, FGF-17, FGF-19, FGF-20, FGF-21, FGF-22, FGF-23 and variants thereof. Each possibility represents a separate embodiment of the present invention.

According to other embodiments, the FGF variant is an N-terminal truncated variant. According to some embodiments, the FGF is an FGF-2 or variants thereof. According to one embodiment, the FGF-2 variant is an FGF-2$^{\Delta 26}$ having a 25 amino acid N-terminal truncation with the Phe26 replaced by a Met residue having the amino acid sequence as set forth in SEQ ID NO: 1:

```
KDPK RLYCKNGGFF LRIHPDGRVD GVREKSDPHI KLQLQAEERG

VVSIKGVCAN RYLAMKEDGR LLASKCVTDE CFFFERLESN

NYNTYRSRKY TSWYVALKRT GQYKLGSKTG PGQKAILFLP MSAKS
```

According to some embodiments, the FGF is an FGF-18 or variants thereof.

According to one embodiment, the FGF18 variant is an FGF-18$^{\Delta 31}$ having a 30 amino acid N-terminal truncation with the Val31 replaced by a Met residue having the amino acid sequence as set forth in SEQ ID NO: 2:

```
MDFRIHVENQ TRARDDVSRK QLRLYQLYSR TSGKHIQVLG

RRISARGEDG DKYAQLLVET DTFGSQVRIK GKETEFYLCM

NRKGKLVGKP DGTSKECVFI EKVLENNYTA LMSAKYSGWY

VGFTKKGRPR KGPKTRENQQ DVHFMKRYPK GQPELQKPFK

YTTVTKRSRR IRPTHPA
```

According to another embodiment, the FGF18 variant is an FGF-18$^{\Delta 33}$ having a 32 amino acid N-terminal truncation with the Phe33 replaced by a Met residue having the amino acid sequence as set forth in SEQ ID NO: 3:

```
MRIHVENQ TRARDDVSRK QLRLYQLYSR TSGKHIQVLG

RRISARGEDG DKYAQLLVET DTFGSQVRIK GKETEFYLCM
```

-continued

```
NRKGKLVGKP DGTSKECVFI EKVLENNYTA LMSAKYSGWY

VGFTKKGRPR KGPKTRENQQ DVHFMKRYPK GQPELQKPFK

YTTVTKRSRR IRPTHPA
```

According to yet another embodiment, the FGF-18 variant is an N-terminal truncated FGF-18$^{\Delta 37}$ having a 36 amino acid N-terminal truncation with the Val37 replaced by a Met residue having the amino acid sequence as set forth in SEQ ID NO: 4:

```
MENQ TRARDDVSRK QLRLYQLYSR TSGKHIQVLG RRISARGEDG

DKYAQLLVET DTFGSQVRIK GKETEFYLCM NRKGKLVGKP

DGTSKECVFI EKVLENNYTA LMSAKYSGWY VGFTKKGRPR

KGPKTRENQQ DVHFMKRYPK GQPELQKPFK YTTVTKRSRR

IRPTHPA
```

According to yet another embodiment, the FGF-18 variant is an N-terminal truncated FGF-18$^{\Delta 51}$ having a 50 amino acid N-terminal truncation with the Gln51 replaced by a Met residue having the amino acid sequence of FGF-18$^{\Delta 51}$ as set forth in SEQ ID NO: 5:

```
MLRLYQLYSR TSGKHIQVLG RRISARGEDG DKYAQLLVET

DTFGSQVRIK GKETEFYLCM NRKGKLVGKP DGTSKECVFI

EKVLENNYTA LMSAKYSGWY VGFTKKGRPR KGPKTRENQQ

DVHFMKRYPK GQPELQKPFK YTTVTKRSRR IRPTHPA
```

According to another aspect, the present invention provides pharmaceutical compositions comprising as an active ingredient a conjugate according to the present invention and a pharmaceutically acceptable carrier or excipient. According to some embodiments, the pharmaceutical composition further comprises a hyaluronic acid. According to some embodiments, the pharmaceutical composition further comprises a conjugate of fibrin(ogen) coupled with a carboxy polysaccharide. According to some embodiments, the pharmaceutical composition further comprises fibrin(ogen).

According to some embodiments, the pharmaceutical compositions may be administered by any suitable route of administration. Suitable routes of administration include, but are not limited to topical, intralesional, intra-articular, intramuscular, intrathecal, intradermal, intramural, intravenous and subcutaneous applications. Each possibility represents a separate embodiment of the present invention. According to some embodiments, the local administration is via injection, or direct instillation in liquid or semi solid formulations. In other embodiments, the local administration may involve direct instillation of solid or semi solid dosage forms such as a depot or an implant or a scaffold comprising the conjugates of the invention.

The pharmaceutical composition comprising as an active ingredient a conjugate according to the present invention and a pharmaceutically acceptable carrier or excipient is suitable for the treatment, repair or regeneration of injured, diseased or traumatized tissue including, but not limited to, tissues such as bone, skin, cartilage, neurons, cardio-vascular tissue types and the like. Each possibility represents a separate embodiment of the present invention.

According to another aspect, the present invention provides a method of treating or repairing injured, diseased, or traumatized tissue selected from the group consisting of: bone, skin, cartilage, neurons, and cardio-vascular tissue types comprising administering to a subject in need thereof a pharmaceutical composition comprising the conjugate of the present invention. According to some embodiments, the injured, diseased, or traumatized tissue is afflicted with at least one indication selected from non-union fractures, osteoarthritis, chronic wounds, burns, spinal cord injury, peripheral nerve injury and peripheral vascular and cardio-vascular disease comprising administering to a subject in need thereof a pharmaceutical composition comprising as an active ingredient a conjugate according to the present invention and a pharmaceutically acceptable carrier or excipient. According to a particular embodiment, the method of the present invention comprises the treatment of osteoarthritis. According to another particular embodiment, the method of the present invention comprises the treatment of spinal disc injury. In further embodiments, the present invention provides the use of the conjugates disclosed herein for cosmetic treatment including soft-tissue augmentation.

According to another aspect, the present invention provides a method of preparing a conjugate comprising an FGF or variant thereof, wherein the FGF or variant thereof is coupled directly to a carboxy polysaccharide. According to another aspect, the present invention provides a method for the preparation of a conjugate comprising an FGF or variant thereof, wherein the FGF or variant thereof is coupled via a linker to a carboxy polysaccharide. According to some embodiments, the present invention provides a method of preparing a triple conjugate comprising an FGF or variant thereof and fibrin(ogen), wherein the FGF or variant thereof and fibrin(ogen) are coupled directly to a carboxy polysaccharide.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
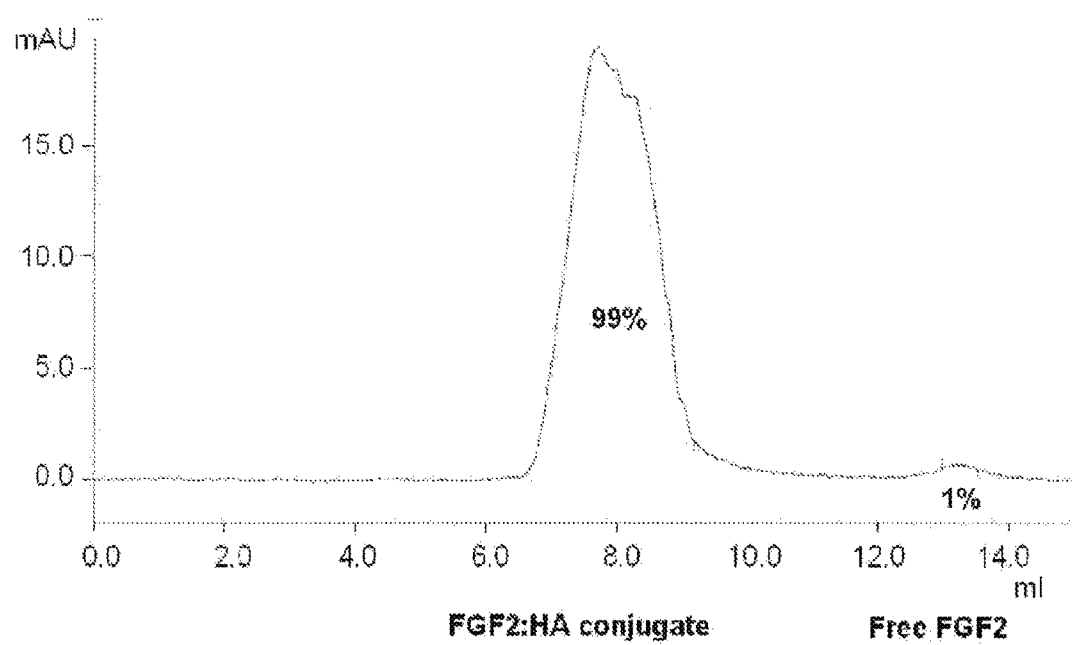
FIG. 1 is a gel filtration analysis and yield calculation of an FGF2-hyaluronic acid conjugate.

The present invention provides conjugates of fibroblast growth factors (FGFs) or variants thereof with carboxy polysaccharides. The conjugates afford improved bioactivity and/or stability of FGFs. The FGFs may be directly bound to the carboxy polysaccharides or indirectly bound via linker moieties. The conjugates may further comprise fibrin(ogen), thereby providing a triple conjugate. Pharmaceutical compositions and methods of preparing the conjugates of the present invention are further disclosed.

The conjugates of the present invention afford the following attributes:
  (i) The conjugates are composed of biocompatible, non-immunogenic natural products.
  (ii) The conjugates are biodegradable, thus deleterious effects associated with accumulation of non-degradable polymeric conjugates in the body are obviated.
  (iii) The conjugates provide improved activity of the FGFs or variant thereof as compared to non-conjugated FGFs.
  (iv) The conjugates provide improved stability of the FGFs or variant thereof as compared to non-conjugated FGFs.
  (v) The activity profile can be further modulated by derivatizing the carboxy polysaccharide (e.g. via partial esterification of the carboxylic and/or the hydroxylic functional groups).

According to one aspect, the present invention provides conjugates comprising FGFs or variants thereof covalently coupled directly or via a linker to a carboxy polysaccharide. According to some embodiments, the conjugates further comprise fibrin(ogen) covalently coupled with the carboxy polysaccharide, thereby providing a triple conjugate. The conjugates of the present invention are water-soluble, therefore can be administered in an aqueous solution or a buffer.

The term "Carboxy polysaccharide" as used herein refers to complex carbohydrates composed of monosaccharides joined by glycosidic bonds and having at least one carboxyl group. The term "carboxy polysaccharide" includes salts thereof, such as sodium or potassium salts, alkaline earth metal salts such as calcium or magnesium salts. Carboxy polysaccharide further includes glycosaminoglycans and anionic polysaccharides. Non-limiting examples of anionic polysaccharides include, but are not limited to, alginate, galactans, galactomannans, and glucomannans.

The term "triple conjugate" as used herein describes a conjugate comprising the three moieties: fibrin(ogen), FGF or variant thereof and carboxy polysaccharide, wherein the fibrin(ogen) and FGF or variant thereof are coupled with the carboxy polysaccharide.

According to some embodiments, the carboxy polysaccharide and FGF or variant thereof are coupled via an amide bond between a carboxylic functional group of the carboxy polysaccharide and an amino functional group of the FGF or a variant thereof. According to some embodiments, wherein the conjugate is a triple conjugate the fibrin(ogen) and FGF or variant thereof are coupled with the carboxy polysaccharide via an amide bond between a carboxylic functional group of the carboxy polysaccharide and an amino functional group of the fibrin(ogen) and FGF or variant thereof. According to some embodiments, the amino functional group of FGF or variant thereof and/or fibrin(ogen) are coupled with an active ester carboxy moiety of the carboxy polysaccharide.

The term "Active esters" or "active ester functional groups" as used herein refer to carboxy moieties of a polysaccharide chemically treated to form a "reactive" ester having higher reactivity with nucleophiles than the corresponding carboxylic acid functionality.

According to some embodiments, the FGF-carboxy polysaccharide conjugate of the present invention comprises a linker through which the FGF or variant thereof is linked to the carboxy polysaccharide moiety. According to some embodiments, wherein the conjugate is a triple conjugate, the fibrin(ogen) is linked with the carboxy polysaccharide moiety via a linker.

The term "linker", as described herein refers to a chemical moiety that serves to link the FGF or variant thereof and/or the fibrin(ogen) to the carboxy polysaccharide while not adversely affecting the therapeutic potential of the FGF or variant thereof and/or fibrin(ogen). According to a specific embodiment, the linker comprises a hydrazido moiety coupled to a maleimido moiety or a vinyl sulfone moiety. Other suitable linkers include, but are not limited to pH-sensitive linkers or enzymatically-cleavable linkers. According to some embodiments, the linker affords the modified release of active FGF or variant thereof and/or fibrin(ogen). According to some embodiments, the carboxy polysaccharide is degraded by an enzyme, thereby providing a modified released of the FGF or variant thereof and/or fibrin(ogen) from the conjugate. According to some embodiments, the carboxy polysaccharide is degraded by enzymes including, but not limited to hyaluronidase. According to some embodiments, the linker and the carboxy polysaccharide are degraded by enzyme(s), thereby providing a modified release of the FGF or variant thereof and/or fibrin(ogen) from the conjugate.

The term "Modified release" in the context of the present invention refers to the rate of release of the active ingredient (FGF or variant thereof and/or fibrin(ogen) from the carboxy polysaccharide. The release profile of active FGF or variant thereof and/or fibrin(ogen) can be controlled by features of the conjugates (e.g. the length of the linker, the degree of carboxy polysaccharide chemical modifications and the like) and/or by physiological or environmental conditions (e.g. digestion of the carboxy polysaccharide moiety using an enzyme). According to one embodiment, the conjugates of the present invention afford the slow/sustained release of active FGF or variant thereof and/or fibrin(ogen). According to another embodiment, the release profile of active FGF provides the delayed onset release of active FGF post administration. According to some embodiments, the interval of the onset after administration is controlled by an agent which provides at least one of: hydrolysis of the carboxy polysaccharide, digestion of the carboxy polysaccharide by an enzyme, degradation of the carboxy polysaccharide (e.g. by reactive oxidative species (ROS)), or degradation of the linker by an enzyme or hydrolysis. Each possibility represents a separate embodiment of the present invention.

According to some embodiments, the FGF or variant thereof moiety of the conjugate is active in its conjugated form. In accordance with these embodiments, the FGF moiety when bound with the carboxy polysaccharide has activity which varies between fully active FGF or variant thereof to partially active FGF or variant thereof. Each possibility represents a separate embodiment of the present invention. According to other embodiments, the FGF or variant thereof moiety of the conjugate is inactive in the conjugated form, but is active upon release from the conjugate. According to a specific embodiment, wherein the FGF or variant thereof is linked with the carboxy polysaccharide via a hydrazido moiety coupled to a maleimido moiety or a vinyl sulfone moiety, the FGF or variant thereof is inactive in the conjugated form but is active upon release from the conjugate.

According to some embodiments, the conjugates provide FGF or variants thereof activity which is substantially similar to non-conjugated free FGF. According to alternative embodiments, the conjugates provide FGF or variants thereof activity of at least 50% of the activity of non-conjugated free FGF or variant thereof. According to some embodiments, the conjugates provide FGF or variants thereof activity of at least 80% of the activity of non-conjugated free FGF or variant thereof.

According to some embodiments, the conjugates of the present invention provide improved activity of the FGF or variant thereof as compared to non-conjugated FGF or variant thereof.

As used herein the term "improved activity" denotes the biological activity of an FGF or variant thereof following administration to a subject to accomplish a therapeutic effect. The term refers to the improved activity of the conjugate of the present invention as compared to the non-conjugated free moieties comprising the conjugate. The biological activity of the FGF can be evaluated following indicated time points of minutes, hours, days, or months from administration.

According to some embodiments, the conjugates of the present invention provide an improved stability of the FGF or variant thereof as compared to non-conjugated FGF or variant thereof.

As used herein the term "improved stability" describes a prolonged time in which the FGF or variant thereof is active following administration to a subject. The term refers to the improved stability of FGF or valiant thereof administered in the conjugated form as compared to non-conjugated FGF or variant thereof. According to some embodiments, the term refers to a prolonged activity of the FGF or variant when administered in the conjugated from as compared to non-conjugated FGF or variant thereof. The stability of the FGF can be evaluated following indicated time points of minutes, hours, days, or months from administration. According to some embodiments, the activity of the FGF or variant thereof is prolonged by conjugation with a carboxy polysaccharide by at least 0.25, 0.5, 1, 2, 3, 4, 5, 6, 7, 8, 9, 10, 20, 30, 40, 50, 60 more days than non-conjugate FGF or variant thereof. According to a specific embodiment, the conjugate provide FGF or variant thereof activity for at least 7 days.

According to some embodiments, the carboxy polysaccharide of the conjugates of the present invention is further coupled with fibrin(ogen), thereby providing a triple conjugate. The fibrinogen as used in the present invention, can originate from any animal species including mammal and avian species, from a recombinant source, or total or partially purified plasma proteins. The fibrinogen component of the conjugate can be obtained by any methodology known in the art. According to one embodiment, fibrinogen includes fibrinogen variants, including the high molecular weight (HMW), the low molecular weight (LMW) and the LMW derivative (LMW') variants.

According to some embodiments, the triple conjugate is water soluble. According to some embodiments, the finbrin (ogen) of the triple conjugate is cleaved by a fibrinogen cleaving agent, thereby producing a water insoluble fibrin clot.

The term "fibrin clot", as used herein refers to a semisolid or solid mass of fibrin generated from the action of a fibrinogen cleaving agent such as thrombin, on fibrinogen. According to some embodiments, the fibrinogen cleaving agent is any agent capable of cleaving fibrinogen including, but not limited to the protease thrombin. According to some embodiments, the fibrin clot can be produced ex vivo or in situ.

According to some embodiments, the water insoluble clot is freeze-dried, thereby producing a porous fibrin matrix or scaffold.

The term "porous fibrin matrix" or interchangeably a "porous fibrin scaffold" is prepared by freeze-drying of the fibrin clot produced from the triple conjugate of the present invention. The terms "lyophilize" or "freeze drying" refer to the preparation of a composition in dry form by rapid freezing and dehydration in the frozen state (sometimes referred to as sublimation). This process may take place under vacuum at reduced air pressure resulting in drying at a lower temperature than required at full pressure.

The carboxy polysaccharides suitable for the formation of the conjugates of the present invention are complex carbohydrates composed of mono-saccharides joined by glycosidic bonds and having at least one carboxyl group. According to additional embodiments, the carboxy polysaccharide is selected from the group consisting of a natural polysaccharide, a synthetic polysaccharide, a semi-synthetic polysaccharide, and combinations thereof. Each possibility represents a separate embodiment of the present invention.

Natural polysaccharides include, but are not limited to, glycosaminoglycans, alginate, fucoidan, galactans, galactomannans, glucomannans, xanthan gum, gellan and Poly sialic acid (PSA). Glycosaminoglycan(s) (GAGs) include, but are not limited to, hyaluronic acid, heparin, chondroitin sulfate, dermatan sulfate, heparan sulfate, keratan sulfate, and combinations thereof. Each possibility represents a separate embodiment of the present invention. Derivatives and salts of the above, including low molecular weight forms of the glycosaminoglycans are intended to be included in the invention.

Semi-synthetic carboxy polysaccharides include, but are not limited to, carboxyalkyl derivatives of cellulose, starch and chitin, for example, carboxy alkylcellulose including carboxy methylcellulose (CMC) and carboxy ethylcellulose (CEC).

According to one embodiment, the carboxy polysaccharide is hyaluronic acid (HA) and its derivatives including, but not limited to, its partial esters with aliphatic, aryliphatic, heterocyclic and cycloaliphatic alcohols. Salt derivatives of HA include, but are not limited to, sodium salts, quaternary ammonium salts and the like, which are considered within the scope of the present invention. Suitable molecular weights of hyaluronic acid and its partial esters range from about $1 \times 10^4$ Daltons to about three million ($3 \times 10^6$) Daltons. According to some embodiments, wherein the carboxy polysaccharide is HA, the digestion of the carboxy polysaccharide by an enzyme is performed by the action of endogenous hyaluronidase(s).

According to some embodiments, the hyaluronic acid (HA) has a molecular weight in the range of about $1 \times 10^4$ Daltons to about $3 \times 10^6$ Daltons. According to some embodiments, the molar ratio of FGF to HA (FGF:HA) may be from 1:1 to 150:1. According to some embodiments, the molar ratio of FGF:HA may be from 1:1 to 100:1. According to some embodiments, the molar ratio of FGF:HA may be from 1:1 to 50:1. According to some embodiments, the molar ratio of FGF to CMC (FGF:CMC) may be from 1:1 to 20:1. According to some embodiments, the ratio between FGF and HA or CMC in the conjugate may vary according to the molecular weight of the HA or CMC. For example, wherein the molecular weight of the HA is 17,000 Dalton, the FGF:HA molar ratio may be from 1:1 to 5:1. In a particular example, wherein the molecular weight of the HA is 17,000 Dalton, the FGF:HA molar ratio is about 3.7:1. In another example, wherein the molecular weight of HA is 74,000 Dalton, the FGF:HA molar ratio may be from 1:1 to 10:1. In a particular example, wherein the molecular weight of the HA is about 74,000 Dalton, the FGF:HA molar ratio is about 2.2:1. In another example, wherein the molecular weight of HA is 132,000 Dalton, the FGF:HA molar ratio may be from 1:1 to 20:1. In a particular example, wherein the molecular weight of the HA is 132,000 Dalton, the FGF:HA molar ratio is about 5.7:1. In another example, wherein the molecular weight of HA is 234,000 Dalton, the FGF:HA molar ratio may be from 1:1 to 25:1. In particular examples, wherein the molecular weight of the HA is 234,000 Dalton, the FGF:HA molar ratio is about 3:1, 5.5:1, 11:1, or about 22:1. In another example, wherein the molecular weight of CMC is 90,000 Dalton, the FGF:CMC molar ratio may be from 1:1 to 10:1.

According to some embodiments, the molar ratio of FGF to HA to fibrin(ogen) (FGF:HA:FBN) in the triple conjugate is from 1:1:0.25 to 150:1:20.

The FGFs suitable for the formation of the conjugates of the present invention are obtained from mammalian or from non-mammalian sources. Examples of sources of FGFs include, but are not limited to, human, bovine, equine, ovine, porcine or rodents. Each possibility represents a separate embodiment of the present invention. The FGFs within the scope of the present invention include FGF-1, FGF-2, FGF-3, FGF-4, FGF-5, FGF-6, FGF-7, FGF-8, FGF-9, FGF-10, FGF-15, FGF-16, FGF-17, FGF-18, FGF-19, FGF-20, FGF-21, FGF-22, FGF-23 and variants thereof. Each possibility represents a separate embodiment of the present invention. Currently preferred FGFs are FGF-2, FGF-18 and variants thereof.

The term "variant" as used herein refers to a polypeptide sequence that possesses some modified structural property of the wild type or parent protein. For example, the variant may be truncated at either the amino (N-) or carboxy (C-) terminus- or both termini or may have amino acids deleted, inserted or substituted. In one embodiment, the FGF variants are N-terminal truncated variants which may retain up to 0 amino acid residues at the N-terminus extending beyond the core domain. Suitable variants are for example those which are disclosed in WO 2008/038287 to some of the inventors of the present invention.

One example of an FGF variant within the scope of the present invention is an FGF-2 variant denoted as FGF-$2^{\Delta26}$, having a 25 amino acid N-terminal truncation with the Phe26 replaced by a Met residue. The amino acid sequence of FGF-$2^{\Delta26}$ is set forth in SEQ ID NO: 1 hereinbelow:

KDPK RLYCKNGGFF LRIHPDGRVD GVREKSDPHI KLQLQAEERG

VVSIKGVCAN RYLAMKEDGR LLASKCVTDE CFFFERLESN

NYNTYRSRKY TSWYVALKRT GQYKLGSKTG PGQKAILFLP MSAKS

Another example of an FGF variant within the scope of the present invention is an FGF-18 variant FGF-$18^{\Delta31}$ having a 30 amino acid N-terminal truncation with the Val31 replaced by a Met residue. It is to be understood that the amino acid numbering includes the signal peptide located at amino acids positions 1-27 of human FGF-18. The amino acid sequence of FGF-$18^{\Delta31}$ is set forth in SEQ ID NO: 2 hereinbelow:

MDFRIHVENQ TRARDDVSRK QLRLYQLYSR TSGKHIQVLG

RRISARGEDG DKYAQLLVET DTFGSQVRIK GKETEFYLCM

NRKGKLVGKP DGTSKECVFI EKVLENNYTA LMSAKYSGWY

VGFTKKGRPR KGPKTRENQQ DVHFMKRYPK GQPELQKPFK

YTTVTKRSRR IRPTHPA

Another example of an FGF variant within the scope of the present invention is an FGF-18 variant FGF-$18^{\Delta33}$ having a 32 amino acid N-terminal truncation with the Phe33 replaced by a Met residue. It is to be understood that the amino acid numbering includes the signal peptide located at amino acids positions 1-27 of human FGF-18. The amino acid sequence of FGF-$18^{\Delta33}$ is set forth in SEQ ID NO: 3 hereinbelow:

```
MRIHVENQ TRARDDVSRK QLRLYQLYSR TSGKHIQVLG

RRISARGEDG DKYAQLLVET DTFGSQVRIK GKETEFYLCM

NRKGKLVGKP DGTSKECVFI EKVLENNYTA LMSAKYSGWY

VGFTKKGRPR KGPKTRENQQ DVHFMKRYPK GQPELQKPFK

YTTVTKRSRR IRPTHPA
```

Another example of an FGF variant within the scope of the present invention is an FGF-18 variant FGF-18$^{\Delta 37}$ having a 36 amino acid N-terminal truncation with the Va137 replaced by a Met residue. It is to be understood that the amino acid numbering includes the signal peptide located at amino acids positions 1-27 of human FGF-18. The amino acid sequence of FGF-18$^{\Delta 37}$ is set forth in SEQ ID NO: 4 hereinbelow:

```
MENQ TRARDDVSRK QLRLYQLYSR TSGKHIQVLG RRISARGEDG

DKYAQLLVET DTFGSQVRIK GKETEFYLCM NRKGKLVGKP

DGTSKECVFI EKVLENNYTA LMSAKYSGWY VGFTKKGRPR

KGPKTRENQQ DVHFMKRYPK GQPELQKPFK YTTVTKRSRR

IRPTHPA
```

Another example of an FGF variant within the scope of the present invention is an FGF-18 variant FGF-18$^{\Delta 51}$ having a 50 amino acid N-terminal truncation with the Gln51 replaced by a Met residue. It is to be understood that the amino acid numbering includes the signal peptide located at amino acids positions 1-27 of human FGF-18. The amino acid sequence of FGF-18$^{\Delta 51}$ is set forth in SEQ ID NO: 5 hereinbelow:

```
MLRLYQLYSR TSGKHIQVLG RRISARGEDG DKYAQLLVET

DTFGSQVRIK GKETEFYLCM NRKGKLVGKP DGTSKECVFI

EKVLENNYTA LMSAKYSGWY VGFTKKGRPR KGPKTRENQQ

DVHFMKRYPK GQPELQKPFK YTTVTKRSRR IRPTHPA
```

The present invention further provides methods for the formation of the conjugates disclosed herein. According to one embodiment, the method comprises the formation of an amide bond between the amino groups of the growth factor and activated carboxylic functions of the carboxy polysaccharide. In the first step, a reactive ester of a carboxy polysaccharide is formed in aqueous solution in the presence of at least one water-soluble activator and at least one alcohol. The solution is preferably pH controlled using a buffer. According to one embodiment, the reaction is performed in a solution having pH 4-8. According to a specific embodiment, the reaction is performed in a solution having pH 5-6. According to some embodiments, the molar ratio between the activator and the carboxy functional groups of the carboxy polysaccharide is about 1:1 to about 8:1. In other embodiments, the molar ratio is about 2:1 to about 4:1. In some embodiments, the molar ratio between the alcohol and the activator is between about 1:1 to about 5:1. In a specific embodiment, the molar ratio is about 1.6:1 to about 1:1.

Suitable activators include, but are not limited to carbodiimides selected from the group consisting of: (1-[3-(dimethylamino)propyl]-3-ethylcarbodiimide hydrochloride (EDC); (1-[3-(dimethylamino)propyl]-3-ethylcarbodiimide methiodide; and 1-cyclohexyl-3-(2-morpholinoethyl)carbodiimide metho-p-toluenesulfonate and any other water or buffer soluble carboxy activator. Each possibility represents a separate embodiment of the present invention. Suitable alcohols within the scope of the present invention include, but are not limited to, aromatic alcohols, substituted aromatic alcohols, aromatic heterocyclic alcohols, substituted aromatic heterocyclic alcohols, N-hydroxylamine, and combinations thereof. In some embodiments, the alcohol is N-hydroxylamine selected from the group consisting of N-hydroxysuccinimide and sulfo-N-hydroxysuccinimide. Each possibility represents a separate embodiment of the present invention.

Following the formation of a reactive carboxy-polysaccharide, the activator is removed. According to one embodiment, at least 80% of the residual activator is removed. According to another embodiment, at least 90% of the residual activator is removed. According to yet another embodiment, at least 95% of the residual activator is removed. In some embodiments, removal of the residual activator is achieved by adding water insoluble resin having affinity to said activator. The water insoluble resin can carry a functional group that chemically reacts or ionically interacts with the activator. The functional group is selected from a carboxy, phosphate and sulfate group. Resins suitable for removing the residual activator include cation exchange resins such as Amberlite® IRC50 and Dowex®50 and polystyrene resin, polyacrylate resin and the like.

Following the removal of the activator, the solution of the activated carboxy polysaccharide is mixed with a solution of FGF under conditions suitable for the formation of carboxy polysaccharide-FGF conjugate. Such conditions may include the presence of a buffer solution at pH which ranges from 6 to 9. The formed conjugate does not comprise a linker. The conjugate may be further purified as is known in the art. According to some embodiments, wherein a triple conjugate comprising fibrin(ogen) (FBN), FGF or variant thereof and a carboxy polysaccharide is synthesized the fibrin(ogen) is mixed with the solution of the activated carboxy polysaccharide and the FGF or variant thereof is added thereafter. According to some embodiments, the FGF or variant thereof is mixed with the solution of the activated carboxy polysaccharide and fibrin(ogen) is added thereafter. According to some embodiments, the FGF or variant thereof and the fibrin(ogen) are mixed simultaneously with the solution of the activated carboxy polysaccharide.

According to another embodiment, the present invention provides an alternative method for the formation of the conjugates discloses herein. In accordance with these embodiments, the method comprises the formation of a carbon-sulfur bond via the Michael addition of the protein's thiol groups to an activated double bond of the Michael acceptor (e.g maleimido functional group)-derivatized carboxy polysaccharide. In the first step, hydrazido-derivatized carboxy polysaccharide (CPS) represented by the formula: CPS—CONHNH$_2$ is formed in the presence of hydrazine and a suitable carboxylic function activator, e.g EDC. Then, the hydrazido-derivatized carboxy polysaccharide is reacted with heterobifunctional linkers that contain an active ester and a Michael acceptor group thus leading to a Michael acceptor-derivatized CPS. Suitable linkers include, but are not limited to, hetero bi-functional linkers which contain N-hydroxysuccinimide (NHS) ester and maleimido functional groups e.g. SMPH (succinimidyl-6-[(β-maleimido propionamido)hexanoate]), BMPS(N-(β-maleimido propyloxy) succinimide ester), GMBS (N-(γ-maleimido butyryloxy) succinimide ester), EMCS(N-(ε-maleimido caproyloxy) succinimide ester) and the like. Each possibility represents a separate embodiment of the invention. Suitable Michael acceptors include, but are not limited to, maleimido, vinyl sulfone, acrylate and metacrylate functions. Each possibility represents a separate embodiment of the invention.

The Michael acceptor-derivatized CPS can be isolated and purified as is known in the art. The degree of substitution with the Michael acceptor can be quantified.

In the next step, a solution comprising the Michael acceptor-derivatized carboxy polysaccharide is reacted with a solution comprising FGF or variant thereof. The pH of both solutions can be controlled by using a buffer, for example at a pH of 6.0-11.0, preferably at a pH of 6.5-9.0 and most preferably at a pH of about 7.4. The formed conjugate can be purified as is known in the art (e.g. by dialysis or FPLC).

The conjugates of the present invention are obtained in exceptionally high yields of 60 to 100%.

Applications

The conjugates of the present invention, as well as the matrix, scaffold or clot produced from the triple conjugate of the present invention are useful for the repair or treatment of diseased or traumatized tissues including, but not limited to bone, skin, disc, cartilage, neurons, cardio-vascular system, and the alike. Each possibility represents a separate embodiment of the present invention. Also included within the scope of the present invention are tissues that exhibit articulated surfaces, such as, spine, shoulder, elbow, wrist, joints of the fingers, hip, knee, ankle, and the joints of the feet. The conjugates of the present invention are suitable for treating any cartilage defect or disorder. The terms "cartilage defect" or "cartilage disorder" as used herein refer to cartilage that has been damaged by disease, injury or trauma including indications such as, but not limited to, rheumatoid arthritis, osteoarthritis and joint injuries. Specifically, the conjugates are useful in the treatment of the degenerative joint disease osteoarthritis, a disease which involves the degradation of joints, including articular cartilage and subchondral bone. Each possibility represents a separate embodiment. The treatment is suitable for an acute injury as well as for a chronic condition requiring prolonged treatment. The conjugates are useful in the treatment of various skeletal disorders including, but not limited to as non-union fractures, joint resurfacing, meniscus repair, craniofacial reconstruction, repair of an intervertebral disc, achondroplasia, osteochondritis dessicans, and spinal cord injury.

The compositions of the present invention are suitable for treating a subject in need thereof, preferably a mammal, particularly a human.

Additional examples of diseases, disorders, or indications that may benefit from treatment with the conjugates of the present invention include, but not limited to chronic wounds, burns, peripheral nerve injury and peripheral vascular and cardiovascular disease. Each possibility represents a separate embodiment of the present invention. The conjugates of the present invention are further useful also for cosmetic application including e.g. soft tissue augmentation.

Pharmaceutical Compositions

The present invention further provides pharmaceutical compositions comprising the conjugates disclosed herein and a pharmaceutically acceptable carrier or excipient.

Suitable carriers or excipients include, but are not limited to, diluents, preservatives, solubilizers, emulsifiers, and/or adjuvants. Suitable diluents include various buffers such as Tris-HCl, acetate, phosphate and the like; detergents and solubilizing agents such as Tween 80 Polysorbate 80 and the like; anti-oxidants such as ascorbic acid, sodium metabisulfite and the like; preservatives such as Thimersol, benzyl alcohol and the like; bulking substances such as lactose, mannitol and the like; as well as other excipients such as water, saline, dextrose, glycerol, ethanol, and the like and combinations thereof. Each possibility represents a separate embodiment of the present invention.

The components of the conjugates of the present invention can be administered as pharmaceutically acceptable salts. Pharmaceutically acceptable salts include the acid addition salts (formed with the free amino groups of the FGF), which are formed with inorganic acids such as, for example, hydrochloric or phosphoric acids, or such organic acids as acetic, oxalic, tartaric, mandelic, and the like. Each possibility represents a separate embodiment of the present invention. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, and the like. Each possibility represents a separate embodiment of the present invention. The pharmaceutical compositions may further comprise a hyaluronic acid. According to some embodiments, the concentration of HA in the pharmaceutical composition is from 0.01% w/v to 80% w/v. According to other embodiments, the concentration of HA in the pharmaceutical composition may be 0.5% (w/v) or within the range of 0.1% (w/v) to 1% (w/v). The pharmaceutical compositions may further comprise fibrinogen or a conjugate of fibrin (ogen) and carboxy polysaccharide. According to some embodiments, the concentration of fibrin(ogen) or fibrin (ogen)-carboxy polysaccharide conjugate in the pharmaceutical composition may be within the range of 0.5% (w/v) to 95% (w/v).

The term "weight/volume" ("w/v") denotes a mass concentration of a solute dissolved in a solution and is calculated as follows: 1 g of solute dissolved in a final volume of 100 mL of solution would be labeled as "1%" or "1% w/v".

According to some embodiments, the composition comprising the triple conjugate is mixed with a fibrinogen-cleaving agent, for example thrombin, to produce a water insoluble fibrin clot.

According to some embodiments, the conjugates, as well as the clot or matrix produced from the conjugates of the present invention can be administered either locally into an area of defect or systemically. The pharmaceutical composition may be formulated for administration in either one or more routes of administrations including, but not limited to topical, intralesional, intra-articular, intramural, intramuscular, intradermal, intrathecal, intravenous or subcutaneous administration.

According to some embodiments, the local administration is via an injection, or direct instillation of liquid or semi solid formulations. According to some embodiments, the local administration may involve direct implantation or instillations of solid or semi solid dosage forms such as a depot or an implant or a scaffold comprising the conjugates of the invention. Any form of preparation of the composition, including but not limited to suspensions of particles, microspheres, microparticles of any desired size and shape might be used and is considered to be within the scope of the present invention.

The following examples are intended to be merely illustrative in nature and to be construed in a non-limiting fashion.

EXAMPLES

Example 1

Preparation of Conjugates Comprising FGFs and Hyaluronic Acid (HA) Via an N-Hydroxysuccinimidyl Active Ester of HA The covalent conjugation of carboxy polysaccharides (HA or CMC) to FGFs was performed by an amide bond formation between the amino groups of the FGFs and activated carboxylic moieties of the carboxy polysaccharides.

Stock Solutions
HA (MW 234 Kd) 1% in DDW
EDC 88 mg/1 ml in DDW (freshly prepared)
NHS 90 mg/1 ml in DDW (freshly prepared)
MES buffer (1 M, pH6)

Preparation of N-hydroxysuccinimidyl Active Ester of HA

HA stock solution (400 µl, 4 mg HA), EDC stock solution (70 µl), NHS stock solution (70 µl), MES buffer (75 µl) and DDW (885 µl) were sequentially added to a plastic tube (5 ml). The clear reaction mixture was agitated gently for 105 minutes at room temperatures to produce an active ester derivative of HA.

In parallel, Amberlite IRC-50/Na$^+$ beads (100 mg) were placed in a plastic tube (5 ml) and soaked in DDW (1.5 ml) for at least 15 minutes. The tube was briefly centrifuged on the bench and the DDW was decanted. The active ester solution was added to the beads and agitated gently for 15 minutes during which residual EDC was removed from the active ester solution by the beads. The mixture was briefly centrifuged on the bench and the active ester solution was decanted. The active ester was immediately used in subsequent conjugation reactions.

Conjugation with FGFs

The solution of active ester was immediately added to a plastic tube (5 ml) containing a mixture of FGF2, FGF18 w.t. or mutant FGF18 (FGF18 v1), denoted herein as FGF-18$^{\Delta 37}$ having the amino acid sequence as set forth in SEQ ID NO: 4 (1 ml, from a stock of 3 mg/ml in PBS), NaCl (0.15 M, 300 µl) and buffer MOPS (1 M, pH7.5, 300 µl). The tube was agitated gently at room temperature overnight. The clear reaction mixture was transferred into a dialysis tubing (MW cutoff 3500 daltons) and dialyzed against PBS for 24 hours (3 exchanges, 1 L each). The dialyzed reaction mixture was stored at 4° C.

The product was analyzed using S-75 gel filtration column in FPLC system. The S-75 column was pre-equilibrated with 1.5 column volumes (36 ml) of PBS containing NaCl (2 M). A 0.5 ml sample of the conjugate's dialyzate (0.5 mg protein) was applied to the column and eluted under isocratic conditions with PBS containing NaCl (2 M) at room temperature. The sample elution profile was monitored by recording the absorbance at 280 nm and was compared to the elution profile of the non-conjugated protein (FGF).

By analyzing both elution profiles, the yield of the conjugate was estimated to be ≥90% (tables 1-3 and FIG. 1). Surprisingly, the yield of conjugation was dramatically decreased when a growth factor other than FGFs was used for conjugation. Specifically, the yield of conjugation of EGF with active ester of HA was very law (table 3). Without being bound by any theory or mechanism of action, FGFs exert a unique affinity to conjugation with carboxy polysaccharides. The conjugation efficiency is independent of the initial concentration of the FGF so long as the molar ratio of FGF:HA is from 22:1 to 3.7:1 and the v/v ratio of MOPS: MES is 4:1. Conjugates of FGFs with carboxy polysaccharides other than HA were prepared in a similar manner.

TABLE 1

The yield of HA-FGF2 conjugates as a function of the reactants molar ratio

| Protein | polymer | Protein:Polymer (moles:moles) | Yield (%) |
|---|---|---|---|
| FGF2 | HA (234 Kd) | 3.5:1 | 99[1] |
| | | 5.5:1 | 99 |
| | | 11:1 | 90 |
| | | 22:1 | 90 |

[1]See FIG. 1. For yield analysis, a sample of the conjugation reaction mixture was applied to S75 gel filtration column in the AKTA 100 FPLC system (GE Healthcare) and eluted under isocratic conditions with PBS containing 2M NaCl at room temperature. The yield of the FGF2:HA conjugate was calculated by peak integration function (area under the curve) using UNICRON 5.2 (GE Healthcare). The yields of the conjugates which were obtained via the maleimido-derivatized HA were calculated using the same analytical procedure and were found to be essentially the same as those obtained by the active ester method.

TABLE 2

Maximal yield of FGF2 conjugates with HA of various molecular weights

| Protein | polymer | Protein:Polymer (moles:moles) | Yield (%) |
|---|---|---|---|
| FGF2 | HA (132 Kd) | 5.7:1 | 90 |
| | HA (74 Kd) | 2.2:1 | 92 |
| | HA (17 Kd) | 0.37:1 | 90 |

TABLE 3

Maximal yields of FGF2 conjugates with carboxy polysaccharides (other than HA) and of HA conjugates with growth factors (other than FGF2)

| Protein | Polymer | Protein:Polymer (moles:moles) | Yield (%) |
|---|---|---|---|
| FGF2 | CMC (90 Kd) | 4:1 | 90 |
| | CMC (250 Kd) | 11:1 | 72 |
| | HAHyd40Ac (234 Kd)[1] | 11:1 | 90 |
| FGF18 | HA (234 Kd) | 2.7:1 | 80 |
| FGF18Δ31[2] | | 2.9:1 | 60 |
| FGF18 Δ33[2] | | 2.9:1 | 66 |
| FGF18 Δ37[2] | | 2.9:1 | 80 |
| FGF18 Δ51[2] | | 3.2:1 | 61 |
| EGF | | 10:1 | 4 |

Table 3:
[1]HA derivative, represented by the formula: HA-CONHNH$_2$, in which 40% of the carboxylic functions were modified into hydrazido groups which were subsequently acetylated.
[2]FGF18 variants in which 31, 33, 37, or 51 amino acids were deleted from the amino-terminal end.

Example 2

Method of Determining the Mitogenic Activity of Conjugates of FGFs with Carboxy Polysaccharide Active Ester on FGFR-Transfected FDCP Cell Lines The FDCP cell line is a murine immortalized, interleukin 3 (IL-3)-dependent cell line of myelocytic bone marrow origin that does not express endogenous FGF Receptors (FGFR). Upon transfection with FGFR cDNA, the FDCP cell line exhibits a dose-dependent proliferative response to FGF that can replace the dependence on IL-3. FGFR transfected FDCP cells can therefore be used to screen various FGFs and FGF derivatives for FGF-dependent cell proliferation. FDCP cells response to various ligands is quantitated by a cell proliferation assay with an XTT reagent (Cell Proliferation Kit, Biological Industries Co.). The method is based on the capability of mitochondrial enzymes to reduce tetrazolium salts into a colorogenic compound, which can be quantitated and is indicative of cell viability.

FDCP cells stably expressing FGFR3-IIIc were grown in "full medium" (Iscove's Medium containing 2 ml glutamine, 10% FCS, 100 µg/ml penicillin, 100 µg/ml streptomycin) supplemented with 5 µg/ml heparin and 10 ng/ml FGF2. Cells were split every 3 days and kept in culture for up to one month. One day prior to the experiment the cells were split. Prior to the beginning of the experiment, the cells were washed ×3 times with full medium (1000 rpm, 8 min). The cells were re-suspended and counted with the VI-cell counter (Beckman Coulter). Twenty thousand ($2 \times 10^4$) cells were added to each well of 96-well plate in 50 µl full medium containing heparin. Full medium was supplemented with heparin and free FGF or FGF conjugates at varying concentrations. Final volume was 100 µl per well. The plate was incubated for 48 hours at 37° C. To assay cell proliferation, 100 µl of PMS reagent was added to 5 ml of XTT reagent and mixed thoroughly (according to manufacturer's protocol). Fifty micro-liters (50 µl) of the latter solution were added into each well. The plates were incubated at 37° C. for 4 hours followed by colorimetric analysis at A490 nm. The results are summarized in Table 4 herein below.

Example 3

Method of Determining the Mitogenic Activity of Conjugates of FGFs with Carboxypolysaccharide Active Ester in Human Primary Articular Chondrocytes (Human PAC)

Isolation of Cells from Cartilage Biopsy

A piece of cartilage tissue was minced into 2 to 4 mm pieces with a sterile scalpel. For each 200 mg of cartilage sample, the digestion mix contained 4000 units of collagenase type II and 1450 PU units pronase E. The digest was in a volume of 4 ml of DMEM-F12 medium. The digestion mixture was added to the tissue sample and left to incubate on a rotator at 37° C., overnight. The cells were centrifuged (1200 rpm, 5-10 min). The medium was aspirated, the cells were washed in 5 ml medium and re-centrifuged. The cells were re-suspended in culture medium and seeded in 25 cm² or 75 cm² flasks at a concentration of approximately $1 \times 10^6$ cells per flask. The cells were incubated in a 5% $CO_2$ incubator at 37° C. The cell medium was replaced every 2-3 days. Cells were counted at different time points using the Vi-Cell XR.

Proliferation Assay of Human PAC

Human PAC were seeded in a 12 well tissue culture multi-well plate at 3000 cells/well in DMEM-F12+10% FBS. In the next day, the cells were treated either with growth medium (control), growth medium plus free FGFs or growth medium plus a conjugate of FGF (see table 4; Example 4). After 4 days, the medium was replaced by a fresh medium+additives as above and incubation was continued for 3 additional days.

Overall, the cells were incubated for 1 week before harvest. Cells were then counted using the Vi-Cell XR cell automatic cell counter. The results are summarized in Example 4 hereinbelow.

Example 4

The Mitogenic Activity of Conjugates of FGFs with Carboxypolysaccharide Active Ester In order to test the mitogenic activity of the conjugates, each conjugate was isolated from the reaction mixture using an FPLC system (AKTA) under conditions specified in Example 1. The mitogenic activity of the conjugates is summarised in Table 4. Measurement of the mitogenic activity using the FGFR-transfected FDCP cell lines assay showed that the $EC_{50}$ of the free proteins were 1 ng/ml, 5 ng/ml, 3.5 ng/ml and 5.5 ng/ml for FGF2, FGF18, FGF18$^{\Delta33}$ and FGF$^{\Delta51}$, respectively. Each value represents an average of duplicate measurements from at least two independent experiments. The conjugates did not lose their mitogenic activity. The cell yield using human PAC assay in the presence of 0.5 ng/ml conjugate, as a percentage of that achieved in the presence of an equal concentration of the free protein is shown in the right column. Each value represents an average of three measurements. FGF18 and FGF18 conjugates were active in higher doses than FGF2 and FGF2 conjugates.

TABLE 4

Mitogenic activity and cell yield in FDCP cell lines and human PAC assays

| Conjugate | | Mitogenic activity | |
|---|---|---|---|
| | | FDCP-R3 | Human PAC |
| Protein | Polymer | (EC50) | (% cell yield) |
| FGF2 | HA (234 Kd) | ≤5 ng/ml | 111 |
| | HA (132 Kd) | ≤5 ng/ml | 135 |
| | HA (74 Kd) | ≤5 ng/ml | N/A |
| | HA (17 Kd) | ≤3 ng/ml | 119 |
| | HAHyd$_{40}$Ac (234 Kd) | ≤5 ng/ml | 97 |
| | CMC (90 Kd) | ≤3 ng/ml | 104 |
| | CMC (250 Kd) | ≤3 ng/ml | 104 |
| FGF18 | HA (234 Kd) | ≤10 ng/ml | 102[1,2] |
| FGF18 Δ33 | | ≤6.8 ng/ml | 82[1,3] |
| FGF18 Δ37 | | N/A | 201[1,3] |
| FGF18 Δ51 | | ≤12.5 ng/ml | N/A |

[1]The assay was performed essentially with porcine primary articular chondrocytes (porcine PAC) which were found to be more responsive to FGF18 than human PAC.
[2]Cell yield in the presence of 50 ng/ml conjugate as a percentage of that achieved in the presence of an equal concentration of free FGF18.
[3]Cell yield in the presence of 200 ng/ml conjugate as a percentage of that achieved in the presence of an equal concentration of the corresponding free ligand.

Example 5

FGF18-HA Conjugate is Stable in Synovial Fluids

Figure 2:
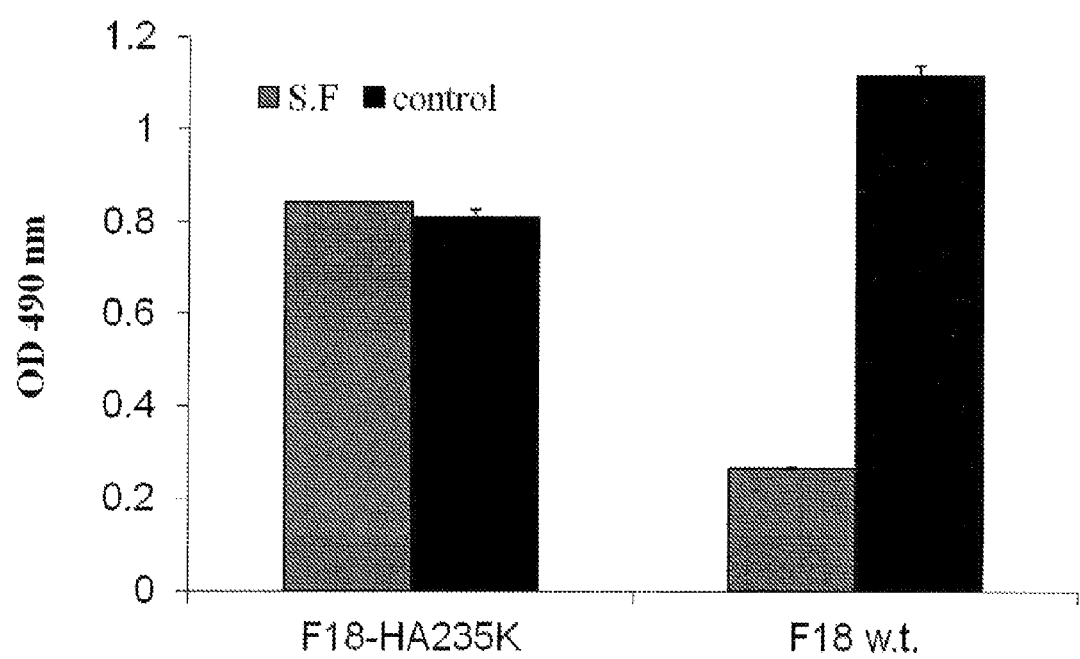
FIG. 2 is a bar graph showing the effect of synovial fluids (S.F) samples containing FGF18 w.t. (F18 w.t.) and a conjugate of FGF18 w.t. with 235 Kd active ester hyaluronic acid (HA) (F18-HA235K) on the proliferation of murine bone marrow-derived cells.

Conjugates of w.t. FGF18 with 235 Kd active ester carboxy polysaccharide were prepared as described in Example 1. The stability of w.t. FGF18 conjugated with HA (F18-HA235K) in synovial fluids was evaluated as follows: 5 ng/ml FGF18-HA (235 Kd) conjugate and equivalent FGF18 w.t. concentration were incubated for 7 days at 37° C. in 90% synovial fluid, or at 4° C. in PBS (control). Following the 7 days incubation, samples were taken and supplemented to murine bone marrow-derived cells for 48 hours. Murine bone marrow-derived proliferation was evaluated using XTT reagent. The activity of FGF18 incubated in synovial fluids was nearly abolished as compared to the control, while the activity of the conjugate remained unaffected (FIG. 2). These results indicate that conjugated FGF18 w.t. is much more stable than non-conjugated FGF18 w.t.

Example 6

The Therapeutic Potential of FGF18-HA Conjugates in an

Conjugates of FGF18 ligands with active ester carboxy polysaccharide were prepared as described in Example 1. The efficacy of non-conjugated FGF18 ligands and FGF18-HA conjugates was evaluated following a destabilization medial meniscus (DMM) model of osteoarthritis in C57BI/6 male mice. Mice were subjected to a surgery to introduce joint instability followed by osteoarthritis. 23 days following surgery, mice were treated with an intra-articular injection of the various treatments. Animals were sacrificed 8 weeks following surgery and operated knees were taken for histology. Isolated left knees that were not subjected to a surgery or injections were used as control. Histology and histochemistry with H&E and Safranin-O staining were used to score cartilage damage.

Figure 3:
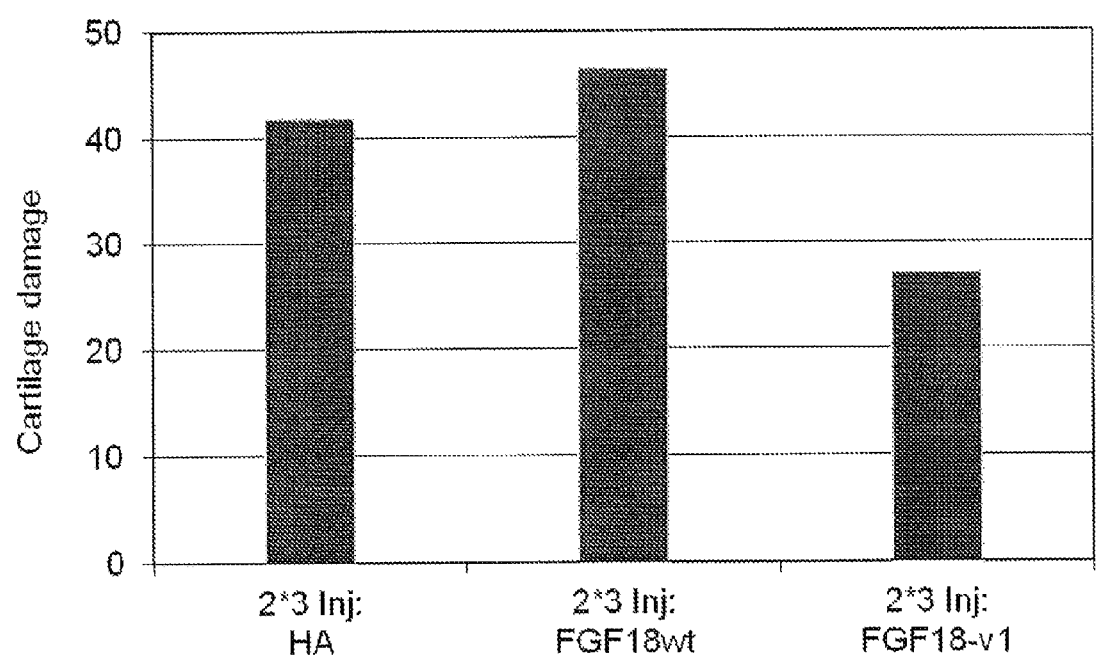
FIG. 3 is a bar graph showing the accumulated cartilage damage score in the medial tibia of mice treated twice a week for up to three weeks with intra-articular injections of HA carrier (0.5%), FGF18 w.t. in HA carrier (0.5%), or mutant FGF18 (FGF18-v1) in HA carrier (0.5%). Treatment was initiated following surgical destabilization of the medial meniscus and onset of osteoarthritis.

The Osteoarthritis Therapeutic Potential of FGF18 w.t. And Mutant FGF18 (v1) Ligands Cartilage damage in the medial tibia was first analyzed in response to an intra-articular injection of non-conjugated FGF18 w.t. and FGF18 mutant (v1) injected twice a week for 3 weeks (0.1 µg/injection, total of 0.6 µg) in 0.5% HA carrier (FIG. 3). Cartilage damage was significantly reduced upon injection with FGF18-v1 while repeated injections of FGF18 w.t. resulted in similar score to that of the ligands' carrier (0.5% HA).

The Therapeutic Potential of FGF18-HA Conjugates.

Figure 4:
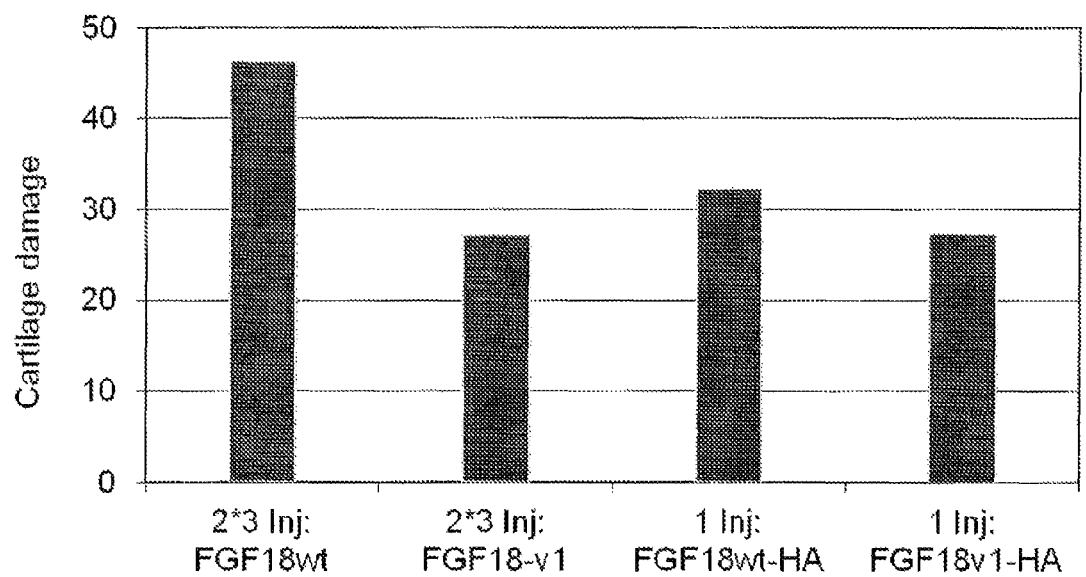
FIG. 4 is a bar graph showing the accumulated cartilage damage score in the medial tibia of mice treated twice a week for up to three weeks with intra-articular injections of FGF18 w.t. in HA carrier (0.5%), or mutant FGF18 (FGF18-v1) in HA carrier (0.5%), or mice treated once with an intra-articular injection of FGF18w.t.-HA or FGF18v1-HA conjugates. Treatment was initiated following surgical destabilization of the medial meniscus and onset of osteoarthritis.

The therapeutic potential of FGF18-HA conjugates was evaluated following the medial meniscus (DMM) model of osteoarthritis in C57BI/6 male mice as described above. Mice were treated with the FGF18 ligands as described above and with a single intra articular injection of 0.5 µg FGF18 w.t.-HA conjugate or FGF18 v1-HA conjugate in 0.5% HA. Treatment with the single injection of FGF18 w.t.-HA conjugate demonstrated considerable decrease in the medial tibia cartilage damage score, exhibiting a 30-40% reduction of cartilage damage score of the FGF18 w.t.-HA as compared to multiple injections of non-conjugated FGF18 w.t. (FIG. 4). Single injection of FGF18 v1-HA conjugate had similar protective effect on cartilage as non-conjugated FGF18 v1 ligand administered in multiple injections. Both non-conjugated and HA conjugate of FGF18 v1 gave a somewhat greater decrease in cartilage damage score indicating the greater potency of the growth factor variant compared to its wild type counterpart.

Example 7

FGF18-HA Conjugates do not Cause Inflammation Upon Intra-Articular Injections

The safety upon intra-articular injections of the conjugates was determined on the medial meniscus (DMM) model of osteoarthritis following a macroscopic analysis of knee. Safety was demonstrated for FGF18-HA conjugates as no swelling and no patellar dislocation were observed in any of the groups that were treated with the HA conjugates.

Example 8

Figure 5:
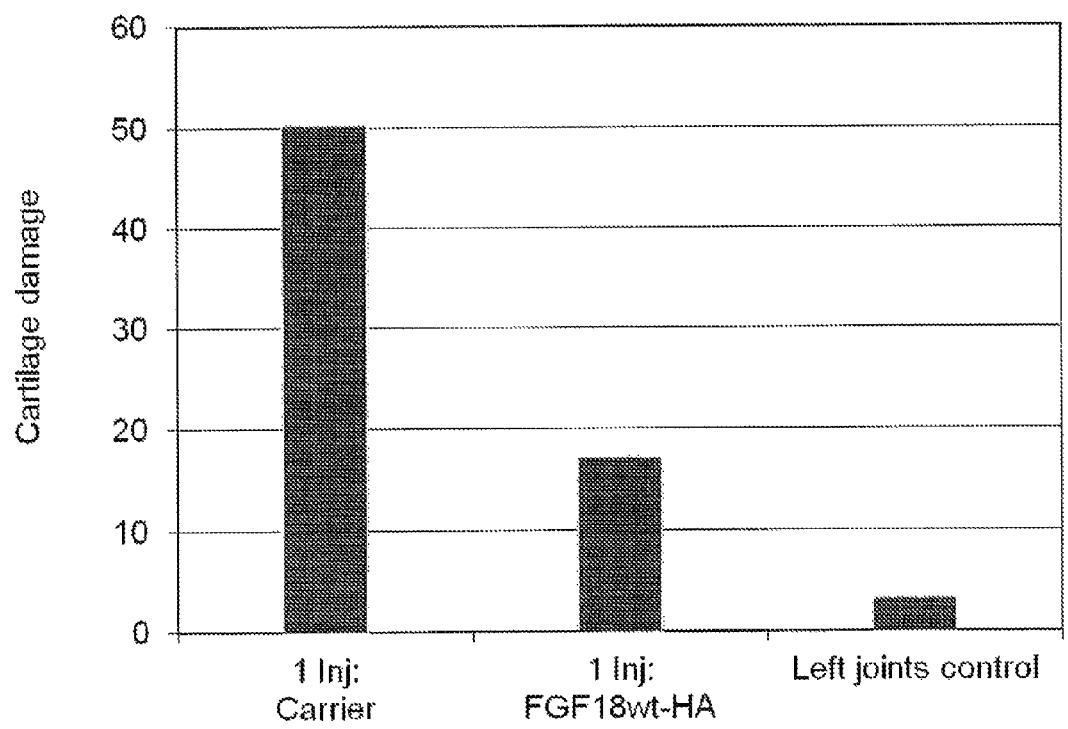
FIG. 5 is a bar graph showing the accumulated cartilage damage score in the medial tibia of mice treated with a single intra-articular injection of FGF18 w.t.-HA conjugate in a fibrinogen-HA conjugate carrier, or fibrinogen-HA conjugate (carrier). A non-surgical, non injected left knee was used as control. Treatment was initiated following surgical destabilization of the medial meniscus and onset of osteoarthritis.

FGF18 w.t.-HA Conjugate Administered in a HA-Fibrinogen Conjugate Carrier has Better Protective Effects on Cartilage in a Murine OA Model Mice were subjected to a DMM surgical procedure. Following 47 days from the surgery, mice were administered with a single injection of either a carrier of fibrinogen-HA conjugate, or a mixture of FGF18 w.t.-HA conjugate and fibrinogen-HA conjugate. A non-surgical left knee was used as control. Animals were sacrificed 10 weeks following surgery and the operated knees were taken for histological analysis. As can be seen in FIG. 5, mice treated with a mixture of FGF18 w.t.-HA conjugate and fibrinogen-HA conjugate demonstrated more than 60% reduction in cartilage damage score as compared to mice treated with the carrier of fibrinogen-HA conjugate alone. Moreover, treatment with a mixture of FGF18 w.t.-HA conjugate and fibrinogen-HA conjugate was demonstrated as more efficient in repair of cartilage than FGF18 w.t.-HA injected in 0.5% HA (FIG. 4).

Example 9

Preparation of Conjugates of FGFs or Variant Thereof and Fibrin(Ogen) with HA Via an N-Hydroxysuccinimidyl Active Ester of HA Triple conjugates of carboxy polysaccharide with FGFs or variant thereof and fibrinogen were prepared with N-hydroxysuccinimidyl active ester of HA as demonstrated in Example 1.

Preparation of FBG-HA-FGF2

Each 4 mg active ester of HA (MW of 3000 kDa) were conjugated with 18 mg FBG (that was dialyzed prior to conjugation against 2L×2 20 mM Citrate pH 7.2+0.9% NaCl over night at 4° C.). For each ml of solution reaction, 100 ng of FGF2 or FGF18 were used (other FGFs or variants thereof can be used for conjugation under the described protocol).

Example 10

The Effect of Fibrin-HA-FGF2 Conjugate on Glycoseaminoglycans (GAGs) Secretion and Proliferation of Osteoarthritic Human Chondrocytes Human chondrocytes isolated from osteoarthritic (OA) knees of patients undergoing total knee replacement were grown in 3 dimensional cultures embedded in a fibrin-HA thrombin containing gels (consent for the study was obtained under an Helsinki ethics committee approved protocol). The 3D gels were immersed in cell growth media. Soluble FGF ligands were either added to the culture media twice a week or pre-conjugated with fibrinogen-HA to form a triple conjugate with FGF2. Cultures were maintained for 1-2 weeks and secreted GAGs and cell proliferation were measured in the culture medium. Alamar blue, a metabolically active cells' indicator and dimethylmethylene blue (DMMB) reagents were used for analysis of cell viability and GAGs secretion, respectively.

Figure 6A:
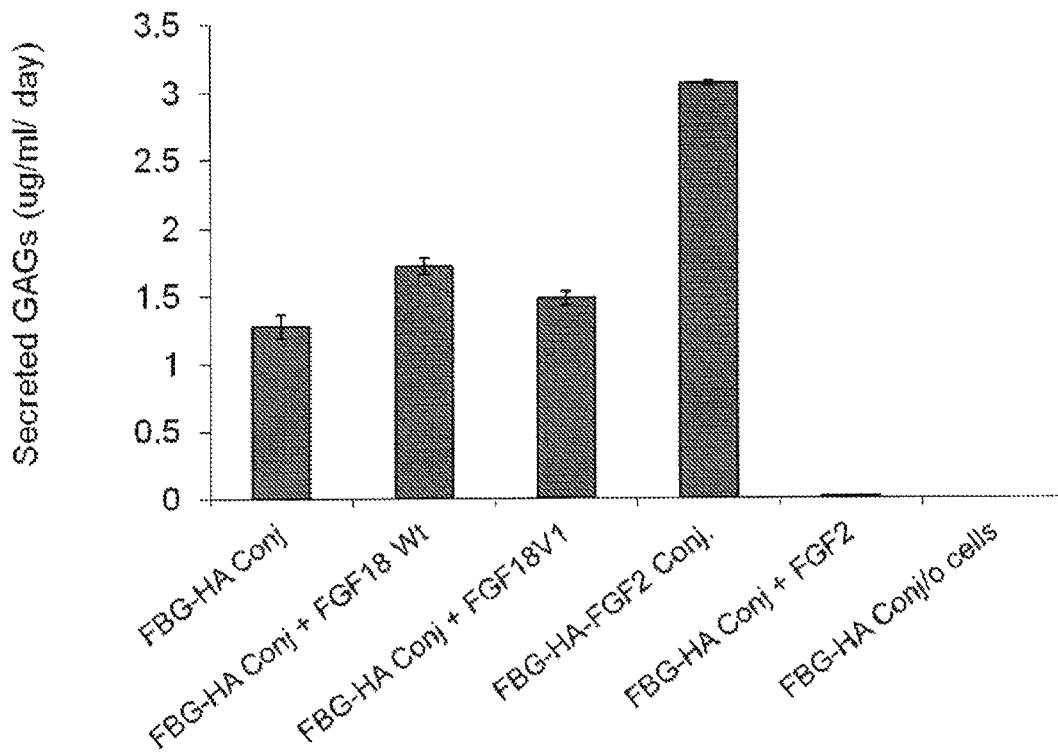
FIG. 6A is a bar graph demonstrating GAG secretion from osteoarthritic chondrocytes obtained from patient A, cultured for 10 days. Osteoarthritic chondrocytes were embedded in 3 dimensional gels of either fibrin(ogen)-HA (FBG-HA) conjugate or fibrin(ogen)-HA-FGF2 (triple conjugate, FBG-HA-FGF2) conjugate. Some cultures of FBG-HA clots were treated bi-weekly with 10 ng/ml of either soluble FGF18 w.t., FGF18v1 or FGF2.
Figure 6B:
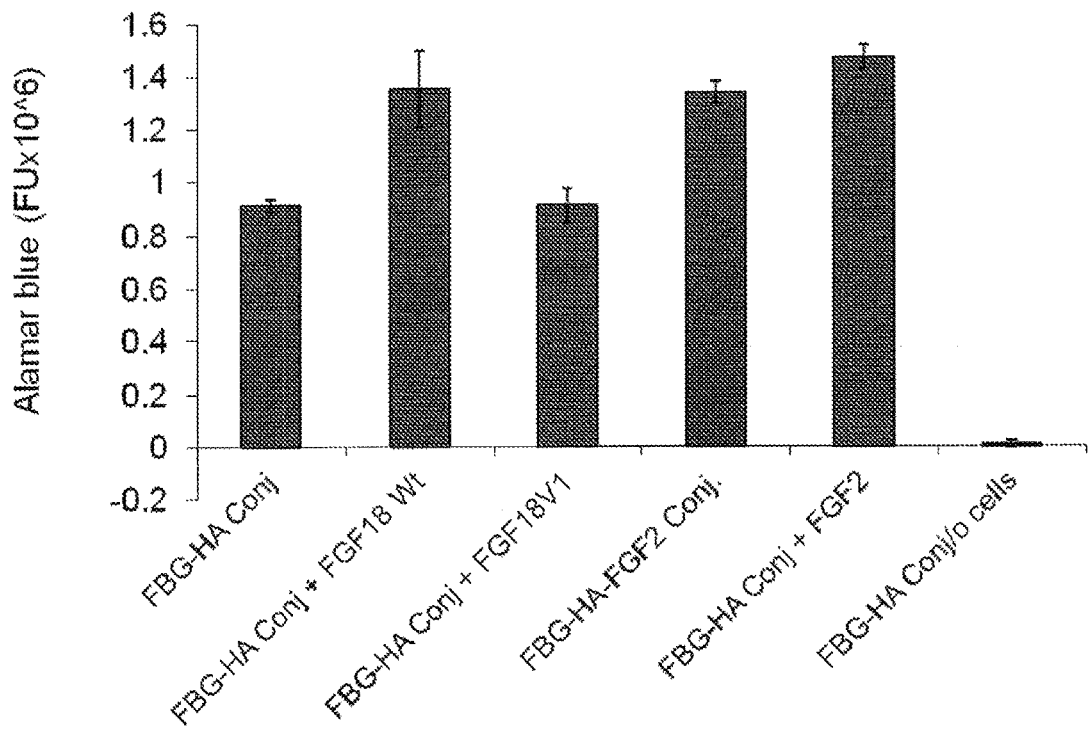
FIG. 6B is a bar graph demonstrating cell metabolism of osteoarthritic chondrocytes obtained from patient A, cultured for 10 days. Osteoarthritic chondrocytes were embedded in 3 dimensional gels of either fibrin(ogen)-HA (FBG-HA) conjugate or fibrin(ogen)-HA-FGF2 (triple conjugate, FBG-HA-FGF2) conjugate. Some cultures of FBG-HA clots were treated bi-weekly with 10 ng/ml of either soluble FGF18 w.t., FGF18v1 or FGF2.
Figure 7A:
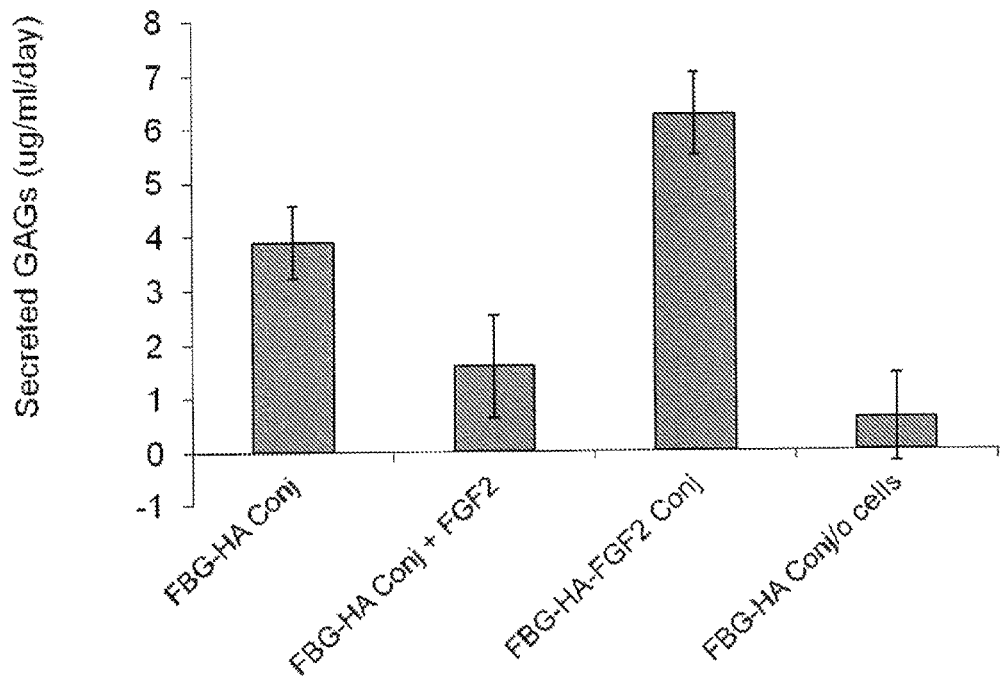
FIG. 7A is a bar graph demonstrating GAG secretion from osteoarthritic chondrocytes obtained from patient B, cultured for 7 days. Osteoarthritic chondrocytes were embedded in 3 dimensional gels of either fibrin(ogen)-HA (FBG-HA) conjugate or fibrin(ogen)-HA-FGF2 (triple conjugate, FBG-HA-FGF2) conjugate. Some cultures of FBG-HA clots were treated bi-weekly with 30 ng/ml of soluble FGF2.
Figure 7B:
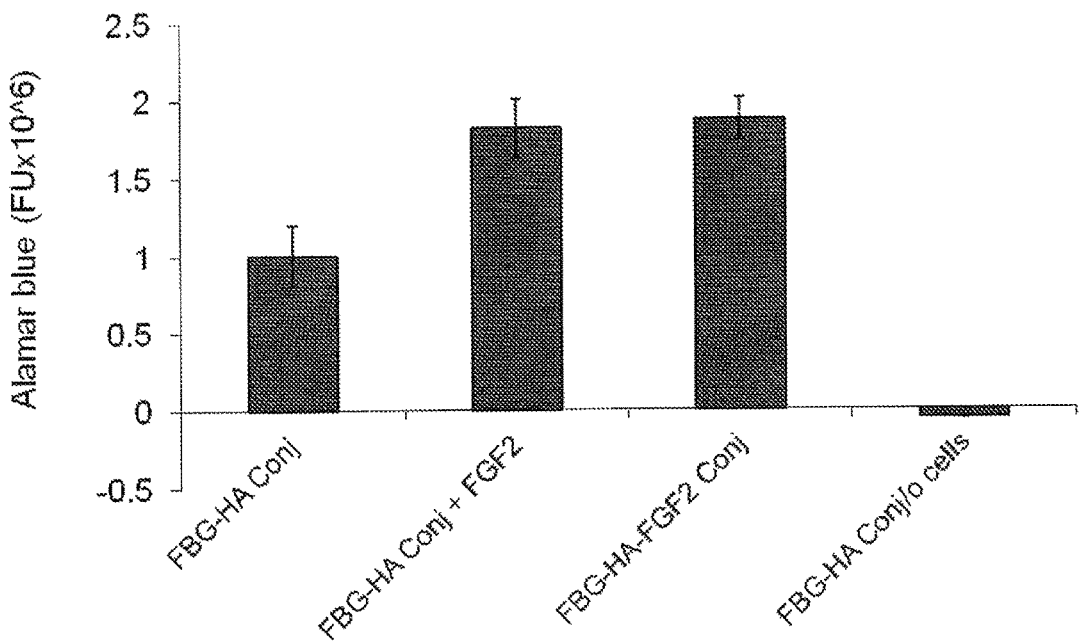
FIG. 7B is a bar graph demonstrating cell metabolism of osteoarthritic chondrocytes obtained from patient B, cultured for 7 days. Osteoarthritic chondrocytes were embedded in 3 dimensional gels of either fibrin(ogen)-HA (FBG-HA) conjugate or fibrin(ogen)-HA-FGF2 (triple conjugate, FBG-HA-FGF2) conjugate. Some cultures of FBG-HA clots were treated bi-weekly with 30 ng/ml of soluble FGF2.

GAGs secretion from OA chondrocytes grown in solid gels prepared from fibrinogen-HA-FGF2 triple conjugate was higher than that from cells embedded in fibrinogen-HA conjugate based gels, with or without the addition of soluble FGF ligands (FIGS. 6A and 7A). This increase was not caused by an increase in cell number evidenced by a similar Alamar blue staining presented in FIGS. 6B and 7B. This observed GAGs secretion indicate of a possible positive effect of immobilized FGF2 on chondrocytes from OA patients that normally have decreased ability to produce extracellular matrix components.

Example 11

Preparation of Maleimido-Labeled Hydrazido-HA

The conjugation of carboxy polysaccharides (HA or CMC) to FGFs was performed by the formation of carbon-sulfur bond via the addition of the protein's thiol groups to the activated double bond of the maleimido function in the maleimido-labeled hydrazido-carboxy polysaccharides. The hydrazido-HA which was used in this example had a MW of 250 Kd and contained 10% or 40% hydrazido groups.

A mixture of solid hydrazido-HA (10 mg, 2.5 pmols hydrazido groups) and DDW (1 ml) was agitated overnight at room temperature to produce a clear solution. Buffer MOPS (1 M.pH7, 150 µl) was then added followed by a solution of SMPH (succinimidyl-6-[(β-maleimido propionamido) hexanoate]) (900 µg, 2.5 µmols) in DMSO (90 µl). SMPH is a hetero bifunctional reagent which contains both a maleimido group and a NHS active ester moiety. Via this active moiety, a covalent bond is formed between the carboxy function of the reagent and the hydrazido groups. Many other structurally related reagents (e.g. BMPS(N-(β-maleimido propyloxy) succinimide ester), GMBS (N-(γ-maleimido butyryloxy) succinimide ester), EMCS(N-(ε-maleimido caproyloxy) succinimide ester) and the like) can be used instead of SMPH as exemplified in Example 6. The reaction mixture was agitated for 4 hours after which it was transferred into a dialysis tubing (MW cutoff 3500 daltons) and dialyzed against DDW for 24 hours (3 exchanges, 1 L each). The dialyzed solution of the maleimido derivative was stored at 4° C. until use. The products were mostly obtained in very high yields, and were purified either by dialysis (to remove byproducts and un-reacted protein) or by FPLC methodology.

Example 12

Quantification of the Maleimido Groups in Maleimido-Labelled Hydrazido-HA

Stock and Sample Solutions

DTT in DDW (0.1 M) containing EDTA (1 mM) (This stock solution is stored at −20° C. under Ar. Under these conditions, the solution is stable for at least 6 months).

Phosphate Buffer (PB) 7.4; (0.1 M, pH7.4) containing EDTA (1 mM)

Phosphate Buffer (PB) 8; (0.1 M, pH8) containing EDTA (1 mM)

DTNB (4 mg) in BP8 (1 ml). This solution is stored at 4° C. in the dark. Under these conditions the solution is stable for 3 months.

A maleimido-labeled hydrazido-HA sample, is prepared by adding 200 µl from the product solution obtained according to Example 5 to PB 7.4 (770 µl).

Procedure

DTT stock solution (30 µl) was mixed with PB 7.4 (570 µl). Then 30 µl of the DTT solution was added to PB 7.4 (970 µl) and incubated for 35 minutes at room temperatures. In parallel, 30 µl of the DTT solution was added to the maleimido sample (970 µl) and incubated for 35 minutes at room temperatures. Subsequently, a blank solution was prepared by mixing 20 µl of the DTNB stock solution with PB 8 (980 µl). The solution was incubated for 15 minutes at room temperatures. 100 µl of the maleimido sample was added to PB 8 (880 µl) followed by DTNB stock solution (20 µl) addition and incubation for 15 minutes. A standard solution was prepared by adding 100 µl of the DTT solution to PB 8 (880 µl) followed by the addition of TNBS stock solution (20 µl) and incubation for 15 minutes. The optical density (OD) of the maleimido sample as well as the OD of the standard solution were read at 412 nm using the blank solution as a reference.

The derivatization degree of the hydrazido-HA is controlled by the ratio maleimido reagent:hydrazido groups. Higher ratios lead to higher derivatization degrees. The maleimido group amount in nmols/1 ml is calculated by using the following equation:

$$nmols/1\ ml = \left[30 - \frac{OD\ \text{maleimido sample} \times 30}{OD\ \text{standard}}\right] \times 50$$

The amount of the maleimido groups in each of the maleimido-labeled hydrazido-HA was determined before use but not later than 24 hours following preparation.

Each conjugate was prepared by using an equivalency ratio of 1:1 maleimido reagent: hydrazido groups and the extent of incorporation of the maleimido group in maleimido-labeled hydrazido-HA is summarized in table 5.

TABLE 5

The percentages of derivatization of the hydrazido and carboxylic moieties

| HA-hyd[1] | Maleimido reagent | Maleimido groups (nmols/1 ml) | $\dfrac{\text{Maleimido groups}}{\text{hydrazido groups}} * 100$ | $\dfrac{\text{Maleimido groups}}{\text{carboxylic groups}} * 100$ |
|---|---|---|---|---|
| HA-hyd (10% hydrazido groups) | BMPS | 288 | 18.4 | 1.84 |
| | GMBS | 235 | 15.9 | 1.59 |
| | EMCS | 235 | 18.8 | 1.88 |
| | SMPH | 300 | 14.4 | 1.44 |
| HA-hyd (40% hydrazido groups) | BMPS | 350 | 22.4 | 8.9 |
| | SMPH | 240 | 27.4 | 10.9 |

[1]Hydrazido-HA (MW 2.5 * 10^5 daltons) represented by the formula: HACONHNH$_2$ in which part of the carboxylic functions were modified into hydrazido groups.

Example 13

Preparation of a Conjugate of FGF2 and HA Via Maleimido-Labeled Hydrazido-HA

A solution of FGF2 in PBS (2.5 ml) was reacted with an aqueous solution of DTT (1 M, 125 µl) for 30 minutes at 37° C. Excess DTT was removed by applying the reaction mixture to a PD-10 desalting column pre-equilibrated with 30 ml of buffer (purged with Ar for 15 minutes before its use) PBS containing 1 mM EDTA. FGF2 (in its reduced form) was eluted from the column using the same buffer (3.5 ml). The eluent contained 277 nmols/1 ml of reactive thiol groups. The reactive thiol concentration was calculated from the protein concentration, taking into account that FGF2 has 2 moles of reactive thiol groups per 1 mole of protein.

Maleimido-labeled hydrazido-HA was prepared by derivatizing hydrazido-HA (MW 250 Kd, 10% hydrazido groups) with SMPH as described in Example 5. The amount of the maleimido groups was found to be 312 nmols/1 ml. Within few hours after its preparation, the maleimido derivative was reacted with the reduced FGF2 using an equivalency ratio of 1:1 maleimido:thiol groups.

A portion of the FGF2 solution (1.5 ml, 415.5 nmols thiol groups) was added to a solution of the maleimido-labeled hydrazido-HA (1.33 ml, 415.5 nmols maleimido groups). A solution of PBS (4.25 ml) containing EDTA (1 mM) was then added to obtain a final protein concentration of 0.5 mg/ml and the clear reaction mixture was incubated for 2 hours at room temperatures. The conjugate solution thus obtained, was stored at −20° C.

A sample of the conjugate (0.5 ml, 0.25 mg protein) was analyzed using S-75 gel filtration column in FPLC system as described above by analyzing the elution profile, it was estimated that the yield of the conjugate was ≥95%.

Example 14

Figure 8:
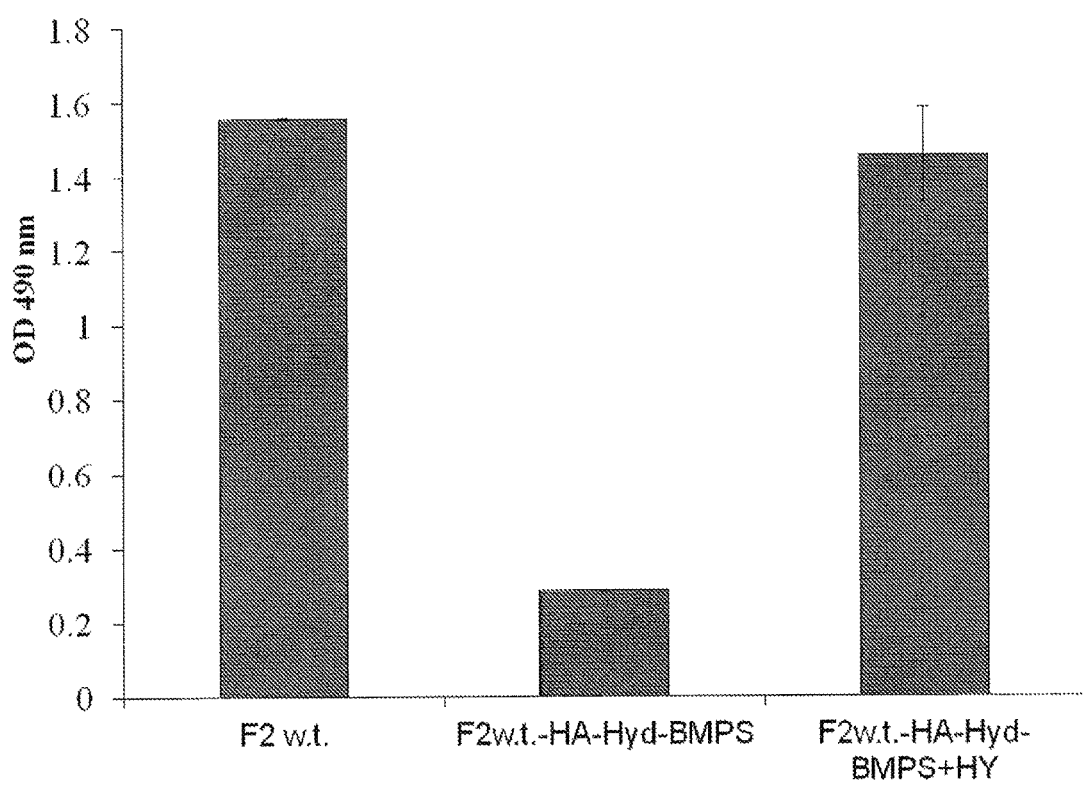
FIG. 8 is a bar graph showing the effect of non-conjugated FGF2 w.t. (F2 w.t.) and a conjugate of FGF2 w.t. with hyaluronic acid-Hydrazido-BMPS (F2w.t.-HA-Hyd-BMPS) in the presence or absence of hyaluronidase (HY) enzyme on cells' proliferation.

The Mitogenic Activity of Conjugates of FGF2 with Various Hydrazido-HA Derivatives The biological activity of the conjugates prepared according to Examples 11-13 with different Maleimido reagents was determined by evaluating the proliferation of FDCP and cells derived from murine bone-marrow. Murine bone marrow-derived cells were incubated with non-conjugated w.t. FGF2, and with HA-hydrazido (containing 38% hydrazido groups) conjugates of FGF2 in the absence or presence of hyaluronidase. The induced proliferation activity of FGF2 in the conjugated form was restored upon digestion by hyaluronidase (FIG. 8). Non-conjugated w.t. FGF2 and a HA-hydrazido FGF2 conjugate incubated in the presence of hyaluronidase significantly induced proliferation of FDCP cells, as compared to HA-hydrazido FGF2 conjugate that was not incubated with hyaluronidase (FIG. 8, and Table 6).

These results indicate that FGF2 can regain its activity after the digestion of hyaluronic acid with hyaluronidase to afford the modified release (unmasking) of active FGF. The activity of FGFs can therefore be controlled using hyaluronidase.

The biological activity of different conjugates containing 10% or 40% hydrazido groups prepared using different maleimido reagents was evaluated also on FDCP cells. The EC$_{50}$ of free FGF2 was found to be 1 ng/ml in this assay. The results are summarized in table 6.

TABLE 6

Mitogenic activity in FDCP cell lines assay

| | | Conjugates EC$_{50}$ (ng/ml) | |
|---|---|---|---|
| HA-hyd[1] | Maleimido reagents | −Hyaluronidase | +Hyaluronidase[2] |
| HA-hyd (10% hydrazido groups) | BMPS | ≥20 ng/ml | ≤5 ng/ml |
| | GMBS | ≥20 ng/ml | ≤5 ng/ml |
| | EMCS | ≥40 ng/ml | ≤5 ng/ml |
| | SMPH | ≥10 ng/ml | ≤5 ng/ml |
| HA-hyd (40% hydrazido groups) | BMPS | ≥15 ng/ml | ≥15 ng/ml |
| | SMPH | ≤5 ng/ml | ≤5 ng/ml |

[1]Hydrazido-HA (MW 2.5 * 10^5 daltons) represented by the formula: HACONHNH$_2$ in which part of the carboxylic functions were modified into hydrazido groups.
[2]Each conjugate sample was digested with 600 units of sheep testicular hyaluronidase per 1 mg of HA for 4 hours at 37° C. and subsequently diluted 1:1000 before being analyzed by the FDCP assay.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A conjugate comprising a fibroblast growth factor (FGF) or a variant thereof covalently coupled directly to a carboxy polysaccharide via an amide bond between a carboxylic functional group of said carboxy polysaccharide and an amino functional group of said FGF or a variant thereof, wherein said carboxy polysaccharide is hyaluronic acid and wherein the FGF is an N-terminal truncated variant of FGF-18 having a sequence selected from the group consisting of SEQ ID Nos. 2-5.

2. The conjugate according to claim 1, further comprising fibrin(ogen), wherein the fibrin(ogen) and FGF or variant thereof are each coupled directly with the carboxy polysaccharide via an amide bond between a carboxylic functional group of said carboxy polysaccharide and an amino functional group of said fibrin(ogen) and FGF or variant thereof.

3. The conjugate according to claim 2, wherein the fibrinogen is cleaved by a fibrinogen cleaving agent, thereby producing a water insoluble fibrin clot.

4. The conjugate according to claim 3, wherein the water insoluble clot is freeze-dried, thereby producing a porous fibrin matrix or scaffold.

5. A pharmaceutical composition comprising a conjugate according to claim 1 and a pharmaceutically acceptable carrier or excipient.

6. The conjugate according to claim 1, formed by coupling the amino functional group of FGF or variant thereof with an active ester carboxy moiety of the carboxy polysaccharide.

7. The conjugate according to claim 1, wherein the molar ratio of FGF to said hyaluronic acid is within the range of 1:1 to 50:1.

8. The conjugate according to claim 1, having improved stability and prolonged activity, in vivo, by at least two fold, when compared to non-conjugated FGF.

* * * * *

SEQUENCE LISTING

<160> NUMBER OF SEQ ID NOS: 5

<210> SEQ ID NO 1
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 1

```
Lys Asp Pro Lys Arg Leu Tyr Cys Lys Asn Gly Gly Phe Phe Leu Arg
1               5                   10                  15

Ile His Pro Asp Gly Arg Val Asp Gly Val Arg Glu Lys Ser Asp Pro
            20                  25                  30

His Ile Lys Leu Gln Leu Gln Ala Glu Arg Gly Val Val Ser Ile
        35                  40                  45

Lys Gly Val Cys Ala Asn Arg Tyr Leu Ala Met Lys Glu Asp Gly Arg
50                  55                  60

Leu Leu Ala Ser Lys Cys Val Thr Asp Glu Cys Phe Phe Phe Glu Arg
65                  70                  75                  80

Leu Glu Ser Asn Asn Tyr Asn Thr Tyr Arg Ser Arg Lys Tyr Thr Ser
                85                  90                  95

Trp Tyr Val Ala Leu Lys Arg Thr Gly Gln Tyr Lys Leu Gly Ser Lys
            100                 105                 110

Thr Gly Pro Gly Gln Lys Ala Ile Leu Phe Leu Pro Met Ser Ala Lys
        115                 120                 125

Ser
```

<210> SEQ ID NO 2
<211> LENGTH: 177
<212> TYPE: PRT
<213> ORGANISM: Artificial Sequence
<220> FEATURE:
<223> OTHER INFORMATION: Synthetic polypeptide

<400> SEQUENCE: 2

```
Met Asp Phe Arg Ile His Val Glu Asn Gln Thr Arg Ala Arg Asp Asp
1               5                   10                  15

Val Ser Arg Lys Gln Leu Arg Leu Tyr Gln Leu Tyr Ser Arg Thr Ser
            20                  25                  30

Gly Lys His Ile Gln Val Leu Gly Arg Arg Ile Ser Ala Arg Gly Glu
        35                  40                  45

Asp Gly Asp Lys Tyr Ala Gln Leu Leu Val Glu Thr Asp Thr Phe Gly
    50                  55                  60

Ser Gln Val Arg Ile Lys Gly Lys Glu Thr Glu Phe Tyr Leu Cys Met
65                  70                  75                  80

Asn Arg Lys Gly Lys Leu Val Gly Lys Pro Asp Gly Thr Ser Lys Glu
                85                  90                  95

Cys Val Phe Ile Glu Lys Val Leu Glu Asn Asn Tyr Thr Ala Leu Met
            100                 105                 110

Ser Ala Lys Tyr Ser Gly Trp Tyr Val Gly Phe Thr Lys Lys Gly Arg
        115                 120                 125

Pro Arg Lys Gly Pro Lys Thr Arg Glu Asn Gln Gln Asp Val His Phe
    130                 135                 140

Met Lys Arg Tyr Pro Lys Gly Gln Pro Glu Leu Gln Lys Pro Phe Lys
145                 150                 155                 160

Tyr Thr Thr Val Thr Lys Arg Ser Arg Arg Ile Arg Pro Thr His Pro
```

```
                165                 170                 175
Ala

<210> SEQ ID NO 3
<211> LENGTH: 175
<212> TYPE: PRT
<213> ORGANISM: Artificial Sequence
<220> FEATURE:
<223> OTHER INFORMATION: Synthetic polypeptide

<400> SEQUENCE: 3

Met Arg Ile His Val Glu Asn Gln Thr Arg Ala Arg Asp Asp Val Ser
1               5                   10                  15

Arg Lys Gln Leu Arg Leu Tyr Gln Leu Tyr Ser Arg Thr Ser Gly Lys
                20                  25                  30

His Ile Gln Val Leu Gly Arg Arg Ile Ser Ala Arg Gly Glu Asp Gly
            35                  40                  45

Asp Lys Tyr Ala Gln Leu Leu Val Glu Thr Asp Thr Phe Gly Ser Gln
    50                  55                  60

Val Arg Ile Lys Gly Lys Glu Thr Glu Phe Tyr Leu Cys Met Asn Arg
65                  70                  75                  80

Lys Gly Lys Leu Val Gly Lys Pro Asp Gly Thr Ser Lys Glu Cys Val
                85                  90                  95

Phe Ile Glu Lys Val Leu Glu Asn Asn Tyr Thr Ala Leu Met Ser Ala
            100                 105                 110

Lys Tyr Ser Gly Trp Tyr Val Gly Phe Thr Lys Lys Gly Arg Pro Arg
        115                 120                 125

Lys Gly Pro Lys Thr Arg Glu Asn Gln Gln Asp Val His Phe Met Lys
    130                 135                 140

Arg Tyr Pro Lys Gly Gln Pro Glu Leu Gln Lys Pro Phe Lys Tyr Thr
145                 150                 155                 160

Thr Val Thr Lys Arg Ser Arg Arg Ile Arg Pro Thr His Pro Ala
                165                 170                 175

<210> SEQ ID NO 4
<211> LENGTH: 171
<212> TYPE: PRT
<213> ORGANISM: Artificial Sequence
<220> FEATURE:
<223> OTHER INFORMATION: Synthetic polypeptide

<400> SEQUENCE: 4

Met Glu Asn Gln Thr Arg Ala Arg Asp Asp Val Ser Arg Lys Gln Leu
1               5                   10                  15

Arg Leu Tyr Gln Leu Tyr Ser Arg Thr Ser Gly Lys His Ile Gln Val
                20                  25                  30

Leu Gly Arg Arg Ile Ser Ala Arg Gly Glu Asp Gly Asp Lys Tyr Ala
            35                  40                  45

Gln Leu Leu Val Glu Thr Asp Thr Phe Gly Ser Gln Val Arg Ile Lys
        50                  55                  60

Gly Lys Glu Thr Glu Phe Tyr Leu Cys Met Asn Arg Lys Gly Lys Leu
65                  70                  75                  80

Val Gly Lys Pro Asp Gly Thr Ser Lys Glu Cys Val Phe Ile Glu Lys
                85                  90                  95

Val Leu Glu Asn Asn Tyr Thr Ala Leu Met Ser Ala Lys Tyr Ser Gly
            100                 105                 110

Trp Tyr Val Gly Phe Thr Lys Lys Gly Arg Pro Arg Lys Gly Pro Lys
```

```
                    115                 120                 125
Thr Arg Glu Asn Gln Gln Asp Val His Phe Met Lys Arg Tyr Pro Lys
        130                 135                 140

Gly Gln Pro Glu Leu Gln Lys Pro Phe Lys Tyr Thr Thr Val Thr Lys
145                 150                 155                 160

Arg Ser Arg Arg Ile Arg Pro Thr His Pro Ala
                165                 170

<210> SEQ ID NO 5
<211> LENGTH: 157
<212> TYPE: PRT
<213> ORGANISM: Artificial Sequence
<220> FEATURE:
<223> OTHER INFORMATION: Synthetic polypeptide

<400> SEQUENCE: 5

Met Leu Arg Leu Tyr Gln Leu Tyr Ser Arg Thr Ser Gly Lys His Ile
1               5                   10                  15

Gln Val Leu Gly Arg Arg Ile Ser Ala Arg Gly Glu Asp Gly Asp Lys
            20                  25                  30

Tyr Ala Gln Leu Leu Val Glu Thr Asp Thr Phe Gly Ser Gln Val Arg
        35                  40                  45

Ile Lys Gly Lys Glu Thr Glu Phe Tyr Leu Cys Met Asn Arg Lys Gly
    50                  55                  60

Lys Leu Val Gly Lys Pro Asp Gly Thr Ser Lys Glu Cys Val Phe Ile
65                  70                  75                  80

Glu Lys Val Leu Glu Asn Asn Tyr Thr Ala Leu Met Ser Ala Lys Tyr
                85                  90                  95

Ser Gly Trp Tyr Val Gly Phe Thr Lys Lys Gly Arg Pro Arg Lys Gly
            100                 105                 110

Pro Lys Thr Arg Glu Asn Gln Gln Asp Val His Phe Met Lys Arg Tyr
        115                 120                 125

Pro Lys Gly Gln Pro Glu Leu Gln Lys Pro Phe Lys Tyr Thr Thr Val
    130                 135                 140

Thr Lys Arg Ser Arg Arg Ile Arg Pro Thr His Pro Ala
145                 150                 155
```